(12) United States Patent
Sarker et al.

US010087132B2

(10) Patent No.: US 10,087,132 B2
(45) Date of Patent: Oct. 2, 2018

(54) SATURATED BRANCHED CHAIN FATTY ACID PRODUCTION METHOD

(71) Applicant: The United States of America, as represented by the Secretary of Agriculture, Washington, DC (US)

(72) Inventors: Majher I Sarker, Wyndmoor, PA (US); Helen N. Lew, Wynnewood, PA (US); Robert A. Moreau, Quakertown, PA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 15/394,015

(22) Filed: Dec. 29, 2016

(65) Prior Publication Data

US 2018/0186716 A1    Jul. 5, 2018

(51) Int. Cl.
| | |
|---|---|
| *C07C 51/36* | (2006.01) |
| *B01J 29/65* | (2006.01) |
| *B01J 29/40* | (2006.01) |
| *B01J 29/70* | (2006.01) |
| *B01J 29/90* | (2006.01) |
| *B01J 38/02* | (2006.01) |

(52) U.S. Cl.
CPC ............. *C07C 51/36* (2013.01); *B01J 29/40* (2013.01); *B01J 29/65* (2013.01); *B01J 29/7007* (2013.01); *B01J 29/90* (2013.01); *B01J 38/02* (2013.01)

(58) Field of Classification Search
CPC ................................. C07C 51/36; B01J 29/40
USPC ......................................................... 554/145
See application file for complete search history.

(56) References Cited

U.S. PATENT DOCUMENTS 9,115,076 B2 *   8/2015   Ngo ...................... C07C 67/333

FOREIGN PATENT DOCUMENTS

WO        WO-2015144232 A1 *  10/2015  .............. B01J 38/52

* cited by examiner

*Primary Examiner* — Deborah D Carr
(74) *Attorney, Agent, or Firm* — John D. Fado; Ediz Yonter; Gail E. Poulos

(57) ABSTRACT

Disclosed herein are processes for converting an unsaturated fatty acid into a saturated branched-chain fatty acid through a zeolite-catalyzed process and methods of economically regenerating and reusing the zeolite catalyst. The processes include subjecting the unsaturated fatty acid to an isomerization reaction to result in a selective conversion of the unsaturated fatty acid into the saturated branched-chain fatty acid. The reaction occurs in the presence of (i) an activated zeolite catalyst, (ii) an effective amount of water, and (iii) optionally an oligomerization reducing agent. The spent zeolite catalyst may be regenerated by heating to create a regenerated zeolite catalyst that is functional for use as the activated zeolite catalyst.

30 Claims, 7 Drawing Sheets

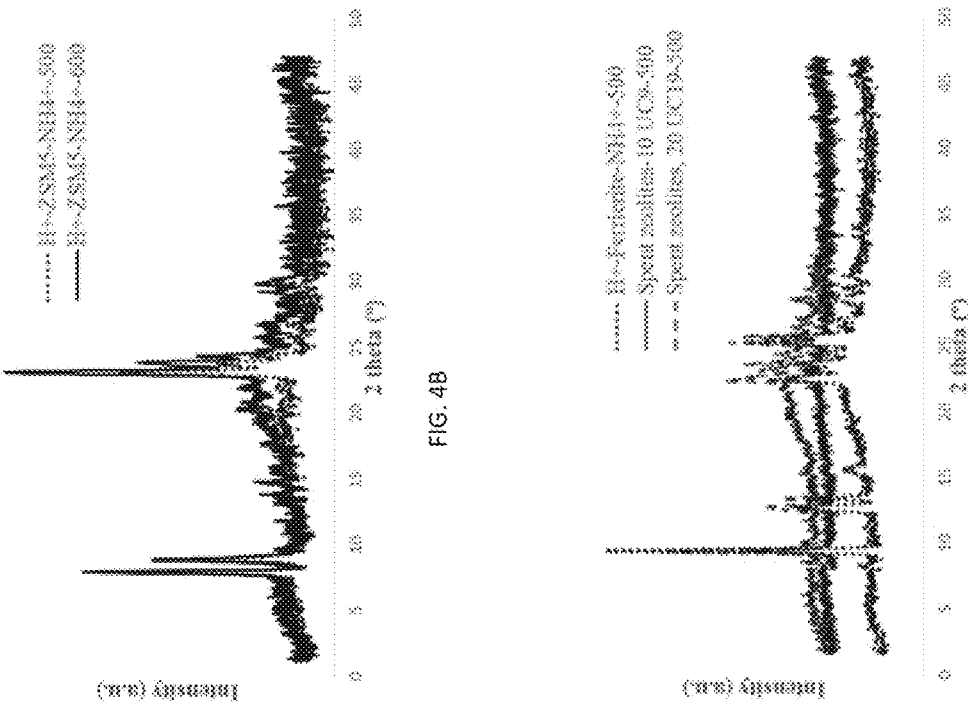
FIG. 4A
FIG. 4B
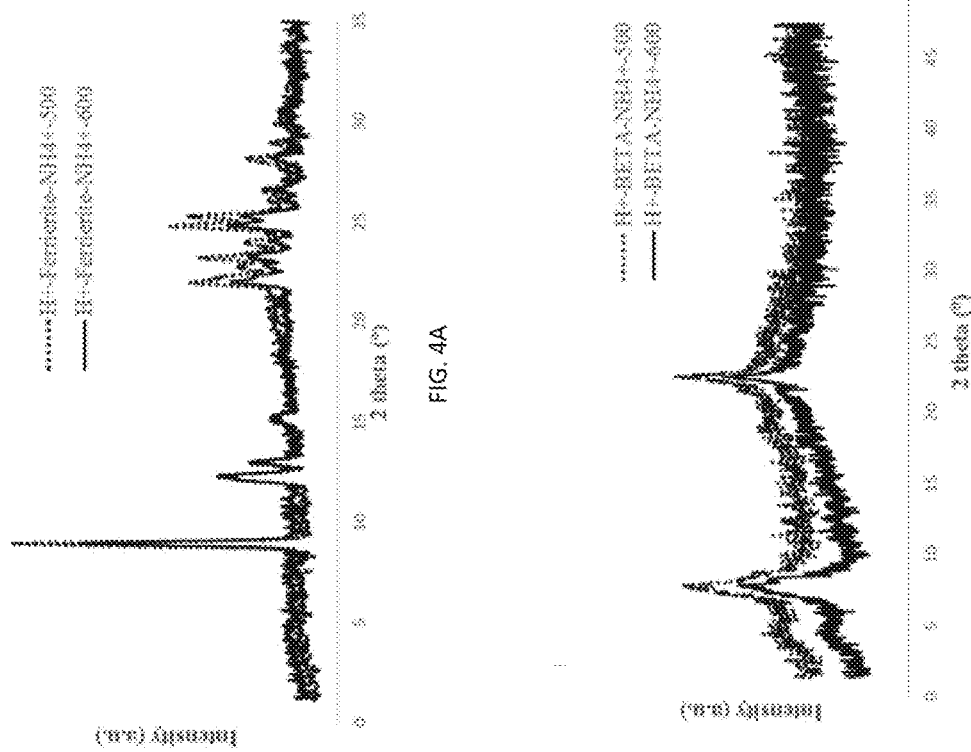
FIG. 4C
FIG. 4D

SATURATED BRANCHED CHAIN FATTY ACID PRODUCTION METHOD

FIELD OF THE INVENTION

The disclosed invention relates generally to novel methods of preparing saturated branched-chain fatty acids. More specifically, the invention relates to novel catalytic processes for the conversion of unsaturated linear chain fatty acids derived from renewable sources to saturated branched-chain fatty acids through the use of acidic zeolite catalysts and the economically favorable regeneration of such catalysts.

BACKGROUND OF THE INVENTION

Commercial scale production of saturated branched-chain fatty acids or alkyl esters thereof using starting materials from renewable sources is gaining enormous interest because of their favorable properties, including better biodegradability as compared to petroleum-based materials, lower toxicity, lower flammability due to their lower vapor pressures, lower melting points, and lower viscosity. These properties make such fatty acids an important feedstock for the production of lubricants, greases, emulsifiers, cosmetic products, surfactants, biodiesel, hydraulic fluids, and many more products. In the petrochemical industry, for example, branched-chain hydrocarbons are consumed for improved octane numbers. Environmental concerns over the use of petroleum-based materials in the lubricant industry have stimulated much research to find suitable alternative materials. In this regard, lubricating fluids derived from renewable fats and oils are of interest because of their purported advantages over petroleum-based materials (Hill, K., Pure Appl. Chem., 79: 1999-2011 (2007)).

Branching induces increased vapor pressures and decreased melting points for the hydrocarbons. Surfactants derived from branched-chain fatty acids show favorable physical properties, including a lower viscosity and improved handling, typically without detriment to intended performance characteristics. Commercial demands for fatty acid products with enhanced performance benefits including higher solubility, ease of handling, better hard water tolerance, improved oxidative stability, lower melting point, lower viscosity, and improved formulations induce enormous industrial interest in such branched-chain fatty acids. There are many commercial products in the market that are derived from renewable resources, such as polylactide polymers and 1,3-propanediol (important intermediates for polymer syntheses) that are derived from biomass sugars by fermentation and are cost-competitive with petroleum-based materials (Carole, T. M., et al., Applied Biochem. and Biotech., 113-116: 871-885 (2004)).

Vegetable oils are also promising candidates as replacements for petroleum-based materials since they have excellent lubricity properties. Although these oils themselves have some commercial use, it is limited due to the presence of double bonds within their fatty acid alkyl chains which lead to oxidative stability problems when used at high temperature. Over the past decades, numerous chemical methods including electrophilic, nucleophilic, oxidative, and metal-catalyzed reactions have been developed that convert the common fatty acids found in renewable fats and oils to novel oleochemical compounds that have improved and/or new properties over the starting fatty acids. For example, chemical processes for the modification of soy oil for use in greases, hydraulic and drilling fluids, and printing inks have been developed (Erhan, S. Z. and M. O. Bagby, J. Am. Oil Chem. Soc., 68(9): 635-638 (1991); Erhan, S. Z., et al., J. Am. Oil Chem. Soc., 69(3): 251-256 (1992); U.S. Pat. No. 5,713,990).

Fatty acids produced from the cleavage of fats and oils derived from renewable sources are typically straight hydrocarbon chains with an even number of carbons. Saturated branched-chain fatty acid isomers, are generally derived from unsaturated fats and oils as a mixture of mono-methyl branched-chain fatty acids. The hydrocarbon chain length generally ranges from 4 to 30 carbons with 12 to 24 carbons being most common. The degree of unsaturation and chain length of a fatty acid are dependent on the triglyceride source from which it is derived. Usually, fatty acids originated from fats have a lower degree of unsaturation than those derived from oils and when the double bonds exist they are more commonly in a cis isomeric configuration.

Existing methods for making saturated branched-chain fatty acids include using clay catalysts, such as bentonite and montmorillonite, and give primarily oligomeric byproducts such as dimers and trimers with much lower yields of the intended fatty acid. No process for reusing clay catalysts has been developed. Another known alternative approach of using metal (e.g., Na+, K+) cationic zeolite catalysts requires acid treatment for its activation which is more costly and less environmentally friendly than the presently disclosed methods (U.S. Pat. Nos. 8,748,641 and 9,115,076). The skeletal isomerization of unsaturated linear chain fatty acids to branched product was previously carried out over a number of acidic catalysts including sulfated zirconia (Hino, M., et al., Solid Super acid Catal., 101: 6439 (1979)); metal-promoted sulfated zirconia (Keogh, R. A., et al., Fuel, 78: 721 (1999); Hsu, C. Y., et al., J. Chem. Soc. Chem. Commun., 22: 1645 (1992); Tomishige, K., et al., Appl. Catal. A, 194: 383 (2000)); silica-supported phosphotungstic heteropolyacids (Tomishige 2000); and acidic alumina-supported noble metal bifunctional catalysts (Juszczyk, W., and Z. Karpinski, Appl. Catal. A, 67: 206 (2001)). Commercially, unsaturated branched-chain fatty acids are also being produced as a byproduct during the dimer acid production process using unsaturated linear chain fatty acids (Berman, L. U., et al. (Eds.), The General Characteristics of Dimer Acid, IN The Dimer Acids, Humko Sheffield Chemical, Memphis, 1975, p. 5). Several clays are also commonly used as catalysts in the acid dimerization process (U.S. Pat. Nos. 3,632,822; 3,732,263; and 6,187,903), where the yield of dimer/trimer acids and monomeric branched-chain fatty acids is 75% and below 20%, respectively. More recently, large-pore zeolites, such as faujasite, beta structure (pore size>6 Angstroms) and mesoporous zeolites (>15 Angstroms), have been used for skeletal isomerization of unsaturated fatty acids (U.S. Pat. Nos. 6,831,184 and 6,723,862; and Ha, L., et al., Applied Catalysis A: General, 356: 52 (2009)) with better yield of branched-chain fatty acids. In these procedures, high catalyst loading, synthesis of expensive in-house zeolite, regeneration of used zeolite, lower conversion, and suppression of dimer acid formation are still issues to be addressed.

There thus exists an industrial need for methods of producing higher yields of saturated branched-chain fatty acids having greater affordability, increased environmental friendliness and economic catalyst activation, and more efficient catalyst regeneration capabilities.

SUMMARY OF THE INVENTION

The present invention accordingly provides novel catalytic processes for the selective conversion of unsaturated linear chain fatty acids to saturated branched-chain fatty acids. Through the use of catalytic acidic zeolites having certain characteristics, high yields of saturated branched-chain fatty acids were obtained from unsaturated linear chain fatty acids derived from renewable sources.

Several embodiments are disclosed herein for the high yield production of saturated branched-chain fatty acids through isomerization reactions of unsaturated linear chain fatty acids using activated zeolite catalysts. In particular, reaction conditions, co-catalyst usage, oligomer formation reducing agents, methods of catalyst regeneration, and zeolite characteristics are disclosed which surprisingly provide more economically feasible and environmentally friendly solutions to produce saturated branched-chain fatty acids through novel processes using unsaturated linear chain fatty acids derived from renewable sources.

In an aspect, the invention is a process for converting an unsaturated fatty acid into a saturated branched-chain fatty acid and/or alkyl ester(s) thereof. The process includes subjecting the unsaturated fatty acid to a skeletal isomerization reaction at a temperature from about 200° C. to about 280° C. for a time range from about 4 to about 24 hours to result in a selective conversion of the unsaturated fatty acid into the saturated branched-chain fatty acid and/or alkyl ester(s) thereof. The skeletal isomerization reaction occurs in the presence of (i) an activated zeolite catalyst, wherein a zeolite catalyst is calcined at a temperature from about 400° C. to about 600° C. from about 1 hour to about 10 hours in a furnace to convert the zeolite catalyst into the activated zeolite catalyst, (ii) an effective amount of water to improve the selective conversion of the unsaturated fatty acid into the saturated branched-chain fatty acid and/or alkyl ester(s) thereof, and (iii) optionally an oligomerization reducing agent. The organic layer is then subjected to a hydrogenation step to remove double bonds within the carbon chains of the fatty acid or ester chains to produce saturated branched-chain fatty acid or ester mixtures. The product including the saturated branched-chain fatty acid is recovered as well as the spent zeolite catalyst. The spent zeolite catalyst is then regenerated by heating to a temperature of about 120° C. to about 500° C. for a time of about 3 hours to about 5 hours to create a regenerated zeolite catalyst that is functional for use as the activated zeolite catalyst.

In another aspect, the invention is a method of regenerating a zeolite catalyst. The method includes calcining the zeolite catalyst at a temperature from about 500° C. to about 600° C. to create an activated zeolite catalyst followed by using the activated zeolite catalyst in a skeletal isomerization reaction to convert an unsaturated fatty acid into a saturated branched-chain fatty acid and/or alkyl ester(s) thereof to create reaction products and a spent zeolite catalyst. The spent zeolite catalyst is recovered and subsequently regenerated by heating the spent zeolite catalyst to a temperature of about 120° C. to about 500° C. for a time of about 3 hours to about 5 hours to create a regenerated zeolite catalyst that is functional for use as the activated zeolite catalyst.

It is an advantage of the invention to provide an activation procedure for zeolites with heat treatment that is more cost effective and environmental friendly than acid treatment thereby preventing acidic waste generation which is costly to handle particularly on an industrial scale.

It is a further advantage of the present invention to provide proprietary technology that efficiently produces high yields saturated branched-chain fatty acids with favorable isomerization reaction conversion rates that are surprisingly selective and avoid excess byproduct generation.

It is an additional advantage of this invention to provide a systematic method for repeatedly regenerating spent zeolite catalysts surprisingly without loss of catalytic performance.

It is another advantage of this invention to provide a systematic method for repeatedly regenerating spent zeolite catalysts that makes the overall catalytic procedures more economically feasible.

Another advantage of the invention is to provide a method of synthesizing isostearic acid using particular zeolite catalysts to achieve products with different physical properties thereby expanding the applications for the isostearic acid products.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

FIG. 4A-4D show XRD pattern of zeolites, where FIG. 4A shows H$^+$-Ferrierite-NH4$^+$-500 and 600, FIG. 4B shows H$^+$-ZSM5-NH4$^+$-500 and 600, FIG. 4C shows H$^+$-BETA-NH4$^+$-500 and 600, and FIG. 4D shows fresh H$^+$-Ferrierite-NH4$^+$-500, spent zeolites-10$^{UC9}$-500, and spent zeolites, 20$^{UC19}$-500 as described below.

FIG. 7A correlates to Table-5A and FIG. 7B correlates to Table-5B.

DETAILED DESCRIPTION OF THE INVENTION

Figure 1:
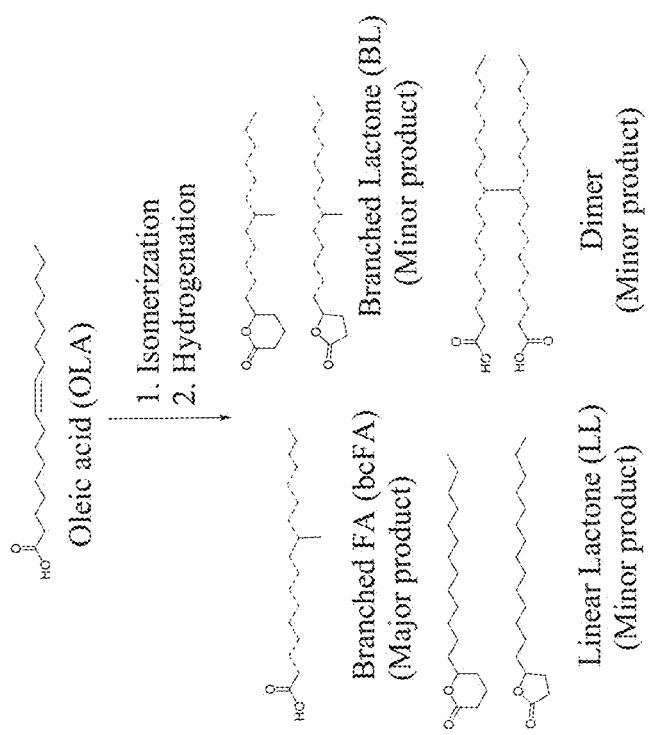
FIG. 1 shows products in skeletal isomerization reaction oleic acid as described below.

Unless herein defined otherwise, all technical and scientific terms used herein generally have the same meaning as commonly understood by one of ordinary skill in the art to which this invention belongs. The definitions below may or may not be used in capitalized form herein and are intended to be used as a guide for one of ordinary skill in the art to make and use the invention and are not intended to limit the scope of the invention. Mention of tradenames or commercial products is solely for the purpose of providing specific information or examples and does not imply recommendation or endorsement of such products.

"Calcination" means a thermal treatment process used herein for the zeolite catalysts used herein in the absence or controlled supply of air or oxygen to bring about a controlled thermal decomposition of the zeolites and activate their catalytic properties.

"Oligomerization Reducing Agent" means a reaction constituent that is capable of reducing (e.g., suppressing) formation of oligomeric byproducts such as dimers and trimers.

"Ratio" means the relative proportion of at least two compounds with respect to one another. Typically, the term "ratio" refers to the relative number of moles (molar ratios) present of each compound or to the mass or volume ratios, as applicable. For example, the silicon to aluminum ratio as used herein means the molar ratio of silicon to aluminum in the zeolite.

"Regeneration" means heating a spent zeolite to reactivate its catalytic properties after being used for a reaction process for repeated reuse in the reaction process of the present invention.

"Renewable Source" means a variety of natural and renewable sources including any source found in nature such as plant and animal products (e.g., vegetable oils and animal fats) or industrial byproducts.

"Saturated Branched-Chain Fatty Acid" means a fatty acid in which there are no double bonds within the fatty acid chain spanning from about 6 to about 30 carbon atoms and at least one hydrogen atom replaced with an alkyl (e.g., methyl, ethyl, propyl, and the like) or other hydrocarbon chain. In embodiments, saturated branched-chain fatty acids are the desired product of the presently disclosed invention.

"Spent Zeolite" means a zeolite catalyst that undergone an activation and reaction cycle and will undergo a subsequent regeneration cycle.

"Unsaturated Branched-Chain Fatty Acid" means a fatty acid in which there is at least one double bond within the fatty acid chain spanning from about 6 to about 30 carbon atoms and at least one hydrogen atom replaced with an alkyl (e.g., methyl, ethyl, propyl, and the like) or other hydrocarbon chain. If the fatty acid chain contains one double bond it is monounsaturated, and if it contains more than one double bond it is polyunsaturated. In embodiments, unsaturated branched-chain fatty acids may be derived from vegetable oils such as soybean oil, sunflower oil, and the like (e.g., oleic acid, palmitoleic acid, erucic acid, elaidic acid, linoleic acid, linolenic acid, and undecenoic acid) as well as various animal fats (e.g., rendered tissue fats obtained from livestock, such as pigs, chickens, and cows as well as dairy products) are used as starting materials in the present invention.

"Zeolite" means crystalline, hydrated aluminosilicates which typically have rigid anionic frameworks containing well-defined channels and cavities. In exemplary embodiments, zeolites are $NH_4^+$-Ferrierite; $NH_4^+$-ZSM-5; $NH_4^+$-BETA.

Several embodiments are disclosed herein related to cycling zeolite catalysts via calcination, reaction to convert an unsaturated fatty acid into a saturated branched-chain fatty acid and/or alkyl ester(s) thereof, followed by recovery of products and spent zeolite catalyst, regeneration of the spent zeolite catalyst, and reuse of the regenerated zeolite catalyst. The disclosed isomerization reactions were surprisingly found to be very effective in producing high yields of, for example, isostearic acid along with lactones and dimer as byproducts as further described in the examples below. In embodiments, the isomerization reactions produce branched-chain free fatty acids depending on the unsaturated bonds of the feedstock and overall reaction conditions including, for example, particularity of the zeolite catalyst; zeolite activation conditions; reaction temperature, pressure, and time; the selected oligomerization reducing agent; and the presence of a co-catalyst such as water or a lower alcohol.

Although the examples below use certain zeolites, many other zeolites with characteristics as herein described are suitable for use in this invention. A selected zeolite typically undergoes a calcination process to activate and prepare it for use as a catalyst in the present invention. The activation procedure with heat treatment is less expensive and more environmentally friendly than acid treatment as the latter generates much acidic waste which is burdensome and costly to handle on an industrial scale. Moreover, heat treatment for activation and regeneration of used catalyst makes the technology of the present invention more cost effective than other known methods, such as systems requiring aqueous acid treatment for activation and proper drying before use (e.g., U.S. Pat. Nos. 8,748,641 and 9,115,076).

In an embodiment, the present invention is a process for converting an unsaturated fatty acid into a saturated branched-chain fatty acid and/or alkyl ester(s) thereof. Production of saturated branched-chain fatty acids are obtained through isomerization reactions of unsaturated linear chain fatty acids using activated zeolite catalysts. In particular, reaction conditions, co-catalyst usage, oligomer formation reducing agents, methods of catalyst regeneration, and zeolite characteristics are disclosed which surprisingly provide more economically feasible and environmentally friendly solutions to produce saturated branched-chain fatty acids through novel processes using unsaturated linear chain fatty acids derived from renewable sources.

According to preferred embodiments, unsaturated fatty acids for use as starting materials in the invention are derived from a variety of renewable sources including any source found in nature such as plant products (e.g., vegetable oils, such as soybean, sunflower, etc.) and animal products (e.g., tallow and as well as various animal fats) or industrial byproducts (e.g., tall oil fatty acid produced during the kraft process of papermaking). For example, fats or triglycerides containing higher levels of monounsaturated chains (i.e., one carbon-carbon double bond) are typically a preferred source of feedstock (e.g., unsaturated free fatty acid) to produce saturated branched-chain fatty acids. Of note is that certain fats or triglycerides should be converted to free fatty acid form (e.g., via hydrolysis methods known in the art) before conversion using the method of the invention. Such unsaturated fatty acids exist in both cis and trans isomeric configurations. Though both configurations may be used in the method of the present invention, the cis configuration is preferred due to its increased reactivity. In embodiments, any combination of these and other sources may be used in the invention. In one embodiment, the unsaturated chain fatty acid is oleic acid, which is a fatty acid that occurs naturally in various animal and vegetable fats and oils. In another embodiment, the unsaturated fatty acid is an unsaturated linear chain fatty acid. Although carbon chain lengths generally range from about 4 to about 30 (e.g., 4 to 30) carbon atoms, about 16 to about 20 (e.g., 16 to 20) carbon atoms is typically the most preferred chain length for use in the present invention. In embodiments, the carbon chain length of unsaturated fatty acid starting material may range from about 12 to about 30 (e.g., 12 to 30) carbon atoms or from about 12 to about 24 (e.g., 12 to 24) carbon atoms. The degree of unsaturation and chain length of these fatty acids are dependent on the source from which it is derived.

When a starting material mixture contains both unsaturated fatty acids or alkyl esters thereof, both branched chain fatty acids and alkyl esters thereof can be produced because both can be isomerized simultaneously. The isomerization of unsaturated fatty acid mixtures is also contemplated herein. The unsaturated fatty acid used as the starting material is generally a fatty acid having unsaturated bonds and a total carbon number of 10 to 25, preferably a total carbon number of 16 to 22. Unsaturated fatty acids having a total carbon number of this range are useful as starting materials for the synthesis herein described for use in, for example, cosmetic bases, fiber treating agents, lubricating oil additives, the like, etc. With respect to the degree of unsaturation (i.e., the number of unsaturated carbon-carbon bonds), any unsaturated fatty acid may be used as long as one or more such bonds are present in the molecule. Specifically, the number of unsaturated bonds is generally 1 to 3, preferably 1. The presence of an unsaturated bond in the molecule causes the formation of a carbocation as an intermediate, thereby facilitating the skeletal isomerization reaction. If a saturated fatty acid is used in large quantities as a starting material, formation of this intermediate carbocation is hampered, thereby making it difficult for isomerization to proceed. Unsaturated fatty acids include oleic acid, palmitoleic acid, erucic acid, elaidic acid, linoleic acid, linolenic acid, and undecenoic acid, which can be derived from beef tallow, palm oil, safflower oil, sunflower oil, tall oil, rapeseed oil, soybean oil, and the like. The mixture that may be used as the starting material is a mixture containing two or more of these unsaturated fatty acids, or a mixture containing one or more of these unsaturated fatty acids and one or more saturated fatty acids such as palmitic and stearic acids, various esters of the aforementioned unsaturated fatty acids, and the like. In the case of a mixture, the content of the above-mentioned unsaturated fatty acids is generally not less than about 40% by weight, preferably not less than about 80% by weight in view of reaction rate and yield. From the viewpoint of reaction selectivity, it is preferable that the above-described starting material contains about 40 to about 100% by weight (e.g., 40 to 100% by weight) of octadecenoic acids, such as oleic acid and elaidic acid.

Alkyl esters of unsaturated fatty acids having a total carbon number of 10 to 25 used as a starting material are those corresponding to the above-described unsaturated fatty acids. That is, alkyl esters of the unsaturated fatty acids exemplified above are used. Although the alkyl moiety is not subject to limitation as to carbon number, its carbon number is normally 1 to 3, preferably 1. Specific examples of alkyl esters include methyl esters, ethyl esters, propyl esters, and butyl esters of the above-mentioned unsaturated fatty acids, with preference given to methyl esters. When a mixture is used as the starting material, a mixture that contains at least one alkyl ester of the above-described fatty acids is used. Specifically, it is a mixture of one or more alkyl esters of these unsaturated fatty acids, or a mixture containing at least one alkyl ester of these unsaturated fatty acids and saturated fatty acids, various esters, etc. In the case of a mixture, the content of alkyl esters of the above-mentioned unsaturated fatty acids is normally not less than about 40% by weight (e.g., not less than 40% by weight), preferably not less than about 80% by weight (e.g., not less than 80% by weight) in view of reaction rate and yield. From the viewpoint of reaction selectivity, it is preferable that the above-described starting material be alkyl esters of unsaturated fatty acids containing about 40 to about 100% (e.g., 40 to 100% by weight) by weight of alkyl esters of octadecenoic acid, such as methyl oleate and methyl elaidate, or a mixture thereof.

In an embodiment, the unsaturated fatty acid is subjected to a skeletal isomerization reaction at a temperature from about 200° C. to 280° C. (e.g., 200° C. to 280° C.) for a time range from about 4 to about 24 (e.g., 4 to 24) hours to result in a selective conversion of the unsaturated fatty acid into the saturated branched-chain fatty acid and/or alkyl ester(s) thereof. It was unexpectedly discovered that certain reactant combinations work best at about 4 (e.g., 4) hours reaction time and other combinations work best at about 24 (e.g., 24) hours. It should be appreciated that reaction conditions may be used which provide for a time range of about 4, 5, 6, 7, 8, 9, 10, 11, 12, 13, 14, 15, 16, 17, 18, 19, 20, 21, 22, 23, or 24 hours as well as any portion of an hour as selected by a skilled artisan for a particular reactant combination. In a preferred embodiment, the unsaturated fatty acid is subjected to the skeletal isomerization reaction at a temperature from about 240° C. to about 260° C. (e.g., 240° C. to 260° C.). It should be appreciated that the reaction temperature may be any temperature or fraction thereof selected from about 240, 241, 242, 243, 244, 245, 246, 247, 248, 249, 250, 250, 252, 253, 254, 255, 256, 257, 258, 259, or 260° C. In another preferred embodiment, the unsaturated fatty acid is subjected to the skeletal isomerization reaction occurs at a temperature of about 260° C. (e.g., 260° C.).

The reaction may be carried out in a closed system where the reaction pressure is generally from about 2 to about 50 kgf/cm² (e.g., 2 to 50 kgf/cm²) to prevent vaporization of reaction constituents as described herein including, for example, water and other low boiling substances in the system including those substances contained in a catalyst. The reaction apparatus used is, for example, an autoclave, because a pressurized reaction system is preferred. The atmosphere in the autoclave is preferably replaced with nitrogen or argon. Other suitable reaction apparatuses may be used as selected by one of ordinary skill in the art.

In all embodiments presented herein, the skeletal isomerization reaction occurs in the presence of an activated zeolite catalyst. It is contemplated that any zeolite can be used in the process, as long as it meets the requirements described herein. Zeolites are crystalline, hydrated aluminosilicates which typically have rigid anionic frameworks containing well-defined channels and cavities. These cavities contain metal cations (e.g., such as $Na^+$, $K^+$, and $NH_4^+$) which are exchangeable, and also neutral "guest" molecules, such as water, which can be removed and replaced. The general formula for a zeolite can be written as follows:

$$M_{x/n}[(AlO_2)_x(SiO_2)_y] \cdot mH_2O$$

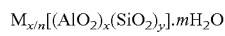

where M is an ion selected from sodium, potassium, or ammonium; n is the valency of the metal ion M which balances the negative charges on the aluminosilicate framework; the ratio y/x represents the silicon-to-aluminum ratio and is a parameter of paramount importance to describe the properties of the zeolite; the sum x+y represents the total number of tetrahedra in a unit cell of the particular zeolite, wherein the microscopic structure of each zeolite is based on the tetrahedron formed between a silicon ($Si^{4+}$) or Aluminum ($Al^{3+}$) cation and four oxygen atoms and are the primary units from which the whole structure is built; and m represents the number of water molecules.

Zeolite catalysts used in the presently disclosed process have a linear pore structure of pore size which is small enough to retard dimerization (e.g., especially in the presence of an oligomerization reducing agent as described herein) and large enough to allow diffusion of fatty acids or alkyl esters thereof. Significant byproduct formation due to oligomerization (e.g., dimer formation) is undesirable because it results in decreased yield of the desired product. Insufficient diffusion of fatty acids, however, is also undesirable because it results in decreased apparent catalyst activity. The preferred mean pore size of the (e.g., microporous) zeolite catalysts is normally about 4 to about 9 Angstroms (e.g., 4 to 9 Angstroms), preferably from about 5 to about 8 Angstroms (e.g., 5 to 8 Angstroms), and more preferably from about 6 to about 7 Angstroms (e.g., 6 to 7 Angstroms). In embodiments, the pore size is selected based on the size of the oligomerization reducing agent or other additives. The pore size must be smaller than the size of such additives to ensure they will not pass through the channel of the zeolite and suppress its activity. The term "linear pore structure" as used herein is a structure wherein pores are formed by at least linear continuous pathways.

The great variety of uses of zeolites is mainly due to particular characteristics of their structures. Many of these characteristics are important to consider for selecting a zeolite for use in the present invention. For example, zeolites are typically gathered in particular structures commonly referred to as "Secondary Building Units" (SBU) (Meier, W. M., Molecular Sieves, Society of Chemical Industry, London, 1968, p. 10). The SBUs are usually used in order to classify the zeolites in groups and are the elementary units from which their topology can be described. The great number of SBUs as well as the variety of combinations that can be made from them enables the building of an almost infinite number of zeolite structures.

Identification of product versatility from different zeolites is another important feature of this invention. For example, the exemplary zeolites herein described result in different composition of isomers for the saturated branched-chain fatty acid product (e.g., isostearic acid). A methyl branching group may appear at different points on the carbon chain and are generally referred to collectively as isostearic acid. The silicon-to-aluminum ratio is a parameter which governs the reactivity of zeolites. For example, when more $AlO_4^-$ groups are present in the zeolite, the greater the negative charge that needs to be balanced, and consequently more positive counter-ions are present in the structure. In addition to providing the electro-neutrality of the structure, the positive ions play an important role in the reactivity of the zeolite due to their location outside of the Al—O—Si framework. As explained in more detail herein, their number is closely related to the number of $AlO_4^-$ units and consequently to the $SiO/Al_2O_3$ ratio. It is now well known that zeolites exhibit proton-donating groups (i.e., Bronsted sites) and electron-accepting functionalities (i.e., Lewis sites) as acid sites (Farneth, W., and R. Gorte, Chemical reviews, 95: 615 (1995)). In a skeletal isomerization reaction, for example, the reactivity of the zeolite depends on the Bronsted properties of the catalyst. In addition, the special layout of the atoms in space is of importance and also governs the reactivity of the zeolite and its catalytic power. The spatial disposition of the atoms and tedrahedra in the zeolites can be characterized by the dimension and the pore size of the microporous structure of the zeolite.

In embodiments, the silicon-to-aluminum ratio (sometimes expressed herein as the $SiO/Al_2O_3$ ratio) in zeolites is an important factor that determines activity toward skeletal isomerization to produce, for example, isostearic acid from linear-chain unsaturated fatty acids. The more $AlO_4^-$ groups in the zeolite, the more positive $H^+$ on activation are needed to neutralize the negatively charged groups, which in turn creates larger active sites. Selection of zeolite with proper $SiO/Al_2O_3$ ratios is a key factor in the method of the invention. In preferred embodiments, selected zeolites have $SiO/Al_2O_3$ ratios in the range of about 17 to about 25 (e.g., 17 to 25) and more preferably in the range of about 20 to about 25 (e.g., 20 to 25).

Figure 2H:
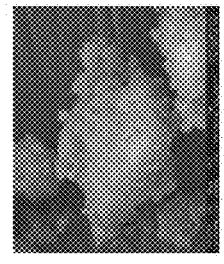
Figure 2J:
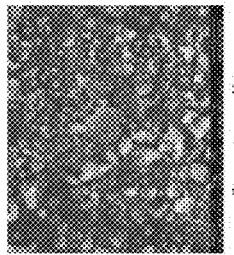
Figure 3:
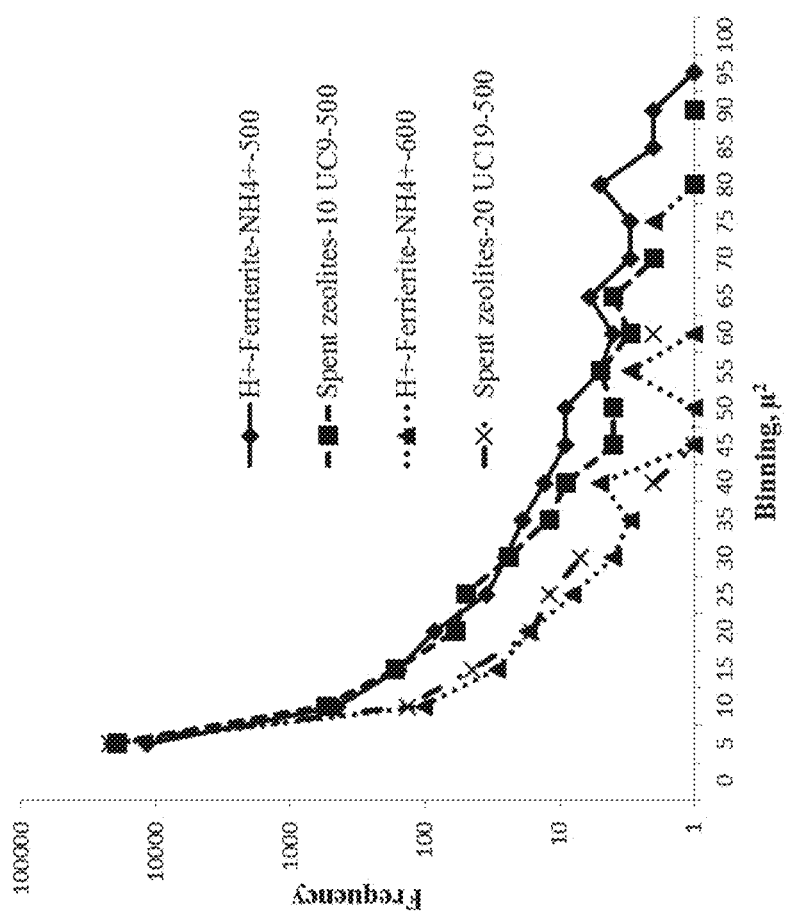
FIG. 3 shows particle size distribution of zeolite samples as described below.

From SEM analysis (FIG. 2A-2F) it can generally be suggested that the morphology of those three zeolites were not widely affected by increasing the calcination temperature from 500° C. to 600° C. On the other hand, spent zeolites used ten times became smaller in size (FIGS. 2H and 2J) which was further supported by particle size distribution analysis (FIG. 3). From EDS analysis (Table 7) it was expected to see no or insignificant changes in Si/Al ratio between the zeolites calcined at different temperature and also between fresh vs spent zeolites revealing no major de-alumination or Al-leaching took place throughout the calcination or reaction procedure. PXRD analysis (FIG. 4A-4C) showed that Ferrierite and ZSM-5 were better crystalline material than BETA when initially calcined at 500° C., but due to high calcination temperature and longer time (600° C. for 24 h), crystallinity dropped in both cases. On the contrary, the level of crystallinity of zeolite used ten times was surprisingly found to be slightly decreased but still comparable to that of fresh staring zeolite (FIG. 4D).

In embodiments herein disclosed, cationic zeolites are used in the skeletal isomerization of unsaturated linear chain fatty acids to saturated branched chain fatty acids. In an embodiment, the selected zeolite is $NH4^+$-Ferrierite ($SiO_2/Al_2O_3$=20). In another embodiment, the selected zeolite is $NH4^+$-ZSM-5 ($SiO_2/Al_2O_3$=23). In a further embodiment, the selected zeolite is $NH4^+$-BETA ($SiO_2/Al_2O_3$=25). In embodiments, more than one zeolite is used in the method of the invention in various amounts. The overall reactivity (i.e., rate of selectivity and/or conversion) of the tested zeolites was found to have the order Ferrierite>ZSM-5>BETA (entry 1 Table 1, entry 3 Table 2, entry 4 Table 3, respectively), which originated from the combination of different factors such as ratio of $SiO_2/Al_2O_3$, density of frame work, crystallinity or proper orientation of atoms in the network, and stability to reaction conditions.

The selected zeolite catalyst must undergo a calcination process to activate its catalytic activity prior to addition into the reaction mixture. During calcination, ammonia, for example, is released from the zeolite catalyst to convert it into a proton cationic zeolite. A main advantage of this process is that acidic components are not used to activate the zeolite for use as a catalyst thus preventing the disadvantage of acidic waste generation. Although any type of heating mechanism known the art may be used for the calcination, the preferred method is a muffle furnace. In an embodiment, the zeolite catalyst is heated and thereby converted into the activated zeolite catalyst at a temperature from about 400° C. to about 500° C. (e.g., 400° C. to 500° C.). Subranges, such as (all in ° C.) about 400 to 405, 405 to 410, 410 to 415, 415 to 420, 420 to 425, 425 to 430, 430 to 435, 435 to 440, 440 to 445, 445 to 450, 450 to 455, 455 to 460, 460 to 465, 465 to 470, 470 to 475, 475 to 480, 480 to 485, 485 to 490, 490 to 495, or 495 to 500, including further subranges or fractional temperatures therein may also be used. In a preferred embodiment, the zeolite catalyst is heated and thereby converted into the activated zeolite catalyst at a temperature of about 450° C. to about 500° C. (e.g., 450° C. to 500° C.). The calcination process takes place for a time range from about 1 hour up to about 10 hours (e.g., 1 to 10 hours). The preferred time range for calcination is about 2 hours up to about 8 hours (e.g., 2 to 8 hours) with about 5 hours (e.g., 5 hours) being the most preferred to achieve the desired selective conversion in the method of the invention.

In embodiments, a co-catalyst is also used in the method of the invention. In one embodiment, an effective amount of water is used as a co-catalyst. In embodiments, a lower alcohol is used as a co-catalyst and is typically exemplified by alcohols having 1 to about 4 (e.g., 1 to 4) carbon atoms. Specifically, methanol, ethanol, propanol, isopropanol, butanol, isobutanol, and the like are preferred, with a greater preference given to those having the same alkyl group as that of the starting fatty acids to be isomerized. As seen in the examples below, the tested zeolites surprisingly showed better performance in terms of selectivity and/or conversion in the presence of specific amounts of water as a co-catalyst.

In preferred embodiments, the amount of co-catalyst used is effective to prevent (e.g., reduce or suppress) lactone formation. The zeolite/co-catalyst combinations generate strategies on how the zeolite based isomerization reaction can be controlled externally with the presence of a small amount of co-catalyst (e.g., water) as the isomerization process takes place inside the cavity of zeolite. For instance, the product selectivity of isostearic acid was increased by 2%, 2.5%, and 10.6% with Ferrierite (entries 1 and 7, Table 1), ZSM5 (entries 5 and 6, Table 2), and BETA (entries 7 and 8, Table 3) zeolites, respectively, due to the presence of an amount of water in the reaction. Along with these tabulated results, it was also noticed that the presence of water promoted the formation of lactones as expected. However, using excess water was found to reduce the reaction selectivity for major products, especially with ZSM5 and BETA zeolites. As seen in the examples below, in the case of ZSM-5 zeolite (entries 1 and 4, Table 2), the product selectivity dropped by 9% as the molar ratio of oleic acid/water was increased from 0.31 to 0.56. Similarly with BETA zeolite, the selectivity dropped by 12.9% for changing the molar ratio of oleic acid/water from 0.25 to 0.56 (entries 4 and 5, Table 3), but no significant change in selectivity was observed with ferrierite zeolite (entries 3 and 5, Table 1). The susceptibility to water depends on the selected zeolite framework. The stepwise decomposition of the zeolite frame work by water was explained by W. Lutz et al. (Lutz, W., et al., Adsorption, 11: 405 (2005)). The more stable framework means better resistance to water. (Zhang, L., et al., J. Am. Chem. Soc., 137: 11810 (2015)). The stability of the framework of the three tested zeolites follows the order Ferrierite>ZSM-5>BETA that can be linked to their largest channel axes which are 5.4×4.2 Angstroms, 5.6×5.3 Angstroms and 7.6×6.4 Angstroms, respectively (Zhang, Z. C., et al., J. of surfactants and detergents, 7: 3 (2004)).

In embodiments, an oligomerization reducing agent may also be used in the method of the invention as oligomer formation (e.g., dimer and trimer) will decrease the formation of the desired isostearic acid product. This invention will help to suppress, for example, dimer formation to more effectively produce high yield of isostearic acid from natural sources, and these natural sources contain poly unsaturated fatty acids which are prone to form dimers instead of the desired isostearic acid product. In embodiments, the oligomerization reducing agent include one or more: amines; phosphines; triarylphosphines; dialkylarylphosphines; trialkylphosphines; and any combinations or mixtures thereof. Exemplary amines include dimethylamine; trimethylamine; diethylamine; trimethylamine; diisopropylamine; triisopropylamine; triphenylamine; diphenylamine; and any combinations or mixtures thereof. Examples of phosphines include methylphosphine; butylphosphine; dibutylphosphine; tributylphosphine; phenylphosphine; diphenylphosphine; and any combinations or mixtures thereof. Example of triarylphosphines include triphenylphosphine; tri-p-tolylphosphine; tri(o-tolyl)phosphine; tri-m-tolylphosphine; trixylylphosphine, tris(p-ethylphenyl)phosphine, tris(p-methoxyphenyl)phosphine, tris(4-fluorophenyl)phosphine; tris(4-methoxyphenyl)phosphine; tris(dimethylamino)phosphine; tris(trimethylsilyl)phosphine; triisopropylphosphine; and any combinations or mixtures thereof. Exemplary dialkylarylphosphines include di-n-butylphenylphosphine; dicyclohexylphenylphosphine; and any combinations or mixtures thereof. Examples of trialkylphosphines include tri-n-butylphosphine; tricyclohexylphosphine; tri-n-octyl-phosphine; trimethyphosphine; triethylphosphine; triisopropylphosphine; tricyclopentylphosphine; and any combinations or mixtures thereof.

In one exemplary embodiment, triphenylphosphine appeared to be very effective to suppress dimer formation in the catalytic systems tested below. The dimer production was reduced by 13.2%, 15.1%, and 10.4% with Ferrierite (entries 1 and 8, Table 1), ZSM-5 (entries 1 and 5, Table 2), and BETA (entries 6 and 7, Table 3) zeolites, respectively, at specific reaction conditions as explained below. A decline in reaction conversion during the process of dimer suppression was also observed unless sufficient reaction time was provided (entries 1 and 5, Table 2).

Figure 7A:
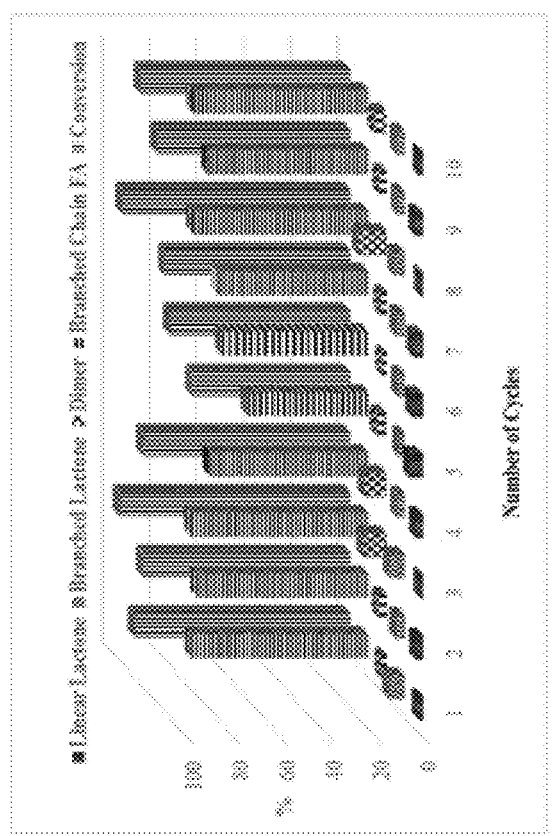
FIG. 7A-7B show systematic regeneration of spent zeolite catalyst as described below.
Figure 7B:
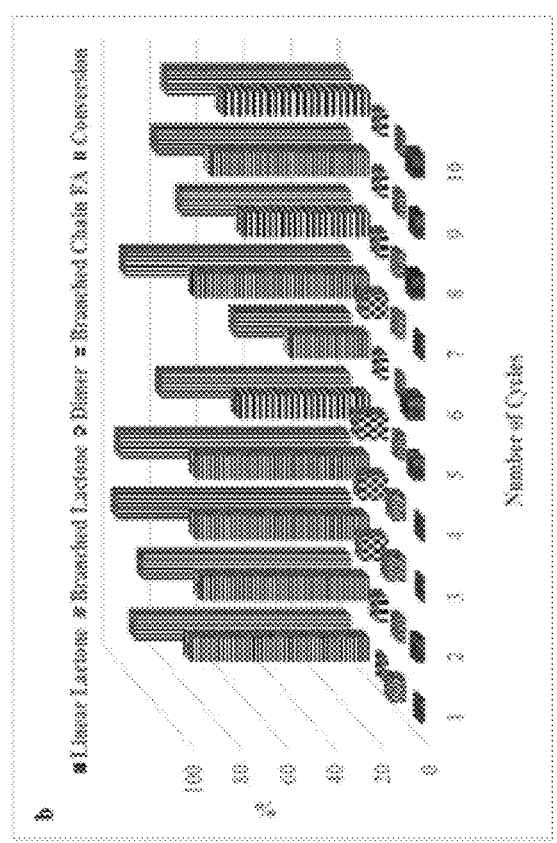

Also of note is that the addition of the oligomerization reducing agent could be effective at any stage of the regeneration process to suppress oligomer formation. For example, the relatively lower efficiency of the spent catalyst at the end of the second series (as seen in cycle 9-10, FIG. 7B) in comparison to the first series (cycle 10, FIG. 7A) could be the result of initial air drying or only one time acid treatment. Therefore, from the experimental results presented below it is likely that for the skeletal isomerization reaction the loss of the catalytic activity of the disclosed zeolites could be caused by a number of factors including (a) deposition of organic residue which can be removed by the heat treatment; (b) loss of protonic ($H^+$) sites caused either by the conversion of Bronsted acid site to Lewis acid site; (c) the acidifying effect of carboxylic groups which could be mitigated with occasional acid treatment or addition of specific amounts of water leading to increased specificity for isostearic acid production; or (d) collapse of the zeolite framework which could be prevented by avoiding excess amount of water and harsh calcination (e.g., higher calcination temperature, such as 600° C., or longer calcination time, such as 5 hours) or reaction conditions.

Furthermore, in the disclosed process, an organic layer including the saturated branched-chain fatty acid product (esters of branched chain saturated fatty acids, when the starting material includes esters of unsaturated fatty acids) is recovered. Removal of zeolite catalyst occurs by filtration, and the residue may also be hydrogenated in an autoclave by a known method, such as the method using a hydrogenation catalyst (e.g., nickel or palladium/carbon), to yield a mixture of crude branched-chain saturated fatty acids (esters of branched chain saturated fatty acids, when the starting material includes esters of unsaturated fatty acids). Then the crude product is purified by removing linear chain components by a known method, such as the compression method, the Emerson method, and the Henkel method (e.g., U.S. Pat. Nos. 2,293,674; 2,421,157; and 2,800,493; J. Am. Oil Chem. Soc., 45, 471 (1968)) or recrystallization method, to yield branched-chain saturated fatty acids (esters of branched chain saturated fatty acids, when the starting material includes esters of unsaturated fatty acids) of high purity. In preferred embodiments, the isomerized fatty acid mixture is subjected to hydrogenation to remove double bonds within the carbon chain of the fatty acid or ester chains to produce saturated branched-chain fatty acid or ester mixtures.

In preferred embodiments, the disclosed process is the selective conversion of the starting material and results in at least about 65% to about 85% selective conversion of the unsaturated fatty acid into the saturated branched-chain fatty acid alkyl ester(s) thereof. In general, a maximum level of selectivity is about 94% because oleic acid feedstock, for example, is about 6% saturated linear chain fatty acid impurity which is not converted to the desired product. Any amount of selective conversion including about 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95% is achievable depending on selection of feedstock and reaction conditions.

For example, considering the product selectivity, reaction conversion and duration it was concluded that entry 1 in Tables 1, 2 and 3 represented the optimized reaction conditions for Ferrierite, ZSM-5 and BETA zeolites respectively to produce isostearic acid. Ten times scale up production of isostearic acid (Table 4) with similar selectivity and conversion to 50 g scale proved the viability of the catalytic system of the invention to be used on a commercial scale.

Upon isolation of the zeolite catalyst from the isomerization process, two different ways (acid treatment or heat treatment) can generally be used to regenerate the spent catalyst. A major advantage of the presently disclosed process is the absence of using an acid treatment to provide the benefit of not creating acid waste disposal issues for industry. It was unexpectedly and surprisingly discovered that regenerating the spent zeolite catalyst by heating the spent zeolite to a temperature of about 120° C. to about 500° C. for a time of about 3 hours to about 5 hours (e.g., 3 to 3.5 hours, 3.5 to 4 hours, 4 to 4.5 hours, or 4.5 to 5 hours) to create the regenerated zeolite catalyst that is functional for use as the activated zeolite catalyst allows reusing the zeolite catalyst for at least about 10 (e.g., 10) cycles. Though shorter regeneration heating times and lower temperatures increases cost effectiveness, higher temperatures closer to 500 C are generally required to, for example, remove residual organic residues trapped within the zeolite channels. It should be appreciated that there was surprisingly and unexpectedly no upper limit discovered to the number of achievable cycles under the time and temperature conditions as herein provided. The regeneration process may take place at any temperature (all in ° C.), such as from about 120 to 150 (e.g., 120 to 150), about 150 to about 200 (e.g., 150 to 200), about 200 to about 250 (e.g., 200 to 250), about 250 to about 300 (e.g., 250 to 300), about 300 to about 350 (e.g., 300 to 350), about 350 to about 400 (e.g., 350 to 400), about 400 to about 450 (e.g., 400 to 450), or about 450 to about 500 (e.g., 450 to 500) according to specific reaction conditions and chosen zeolite(s) as may be determined by a skilled artisan.

In exemplary embodiments, techniques for regenerating spent zeolite catalyst include catalyst-TPP combinations to make the disclosed technology more economically feasible for various levels (e.g., small scale or large scale) of saturated branched-chain fatty acid production. For example, combining effects of $H^+$-ZSM-TPP and $H^+$-BETA-TPP have been reported to provide alternative options for producing isostearic acid from unsaturated linear chain fatty acid.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

EXAMPLES

For the disclosed examples, reagents were laboratory grade oleic acid (91.2 wt % C18:1; 6.1 wt % C18:2; 2.7 wt % saturated fatty acid); triphenylphosphine (TPP), sulfuric acid ($H_2SO_4$), methanol (MeOH); ethylacetate ($CH_3COOC_2H_5$); and hexane ($C_6H_{14}$) purchased from Aldrich Chemical (Milwaukee, Wis.). Three ammonium cationic zeolites ($NH4^+$-Ferrierite, $NH4^+$-ZSM-5, and $NH4^+$-BETA) were purchased from Zeolyst International Co. (Conshohocken, Pa.) and palladium on carbon (5 wt % Pd/C) was purchased from Pressure Chemical Co. (Pittsburgh, Pa.). All other reagents used were commercially available and high purity.

Zeolite catalyst treatment: The three ammonium cationic zeolites were calcined at 500° C. for 5 hours in a furnace to convert them into the protonated form (i.e., activated form) of $H^+$-Ferrierite-$NH4^+$-500, $H^+$-ZSM5-$NH_4^+$500, and $H^+$-BETA-$NH_4^+$-500, respectively, which was required for the acid catalytic isomerization reaction. To determine the impact of calcination temperatures on catalytic activity, the zeolites were also calcined at 600° C. for 24 hours to produce the protonated form of $H^+$-Ferrierite-$NH4^+$-600, $H^+$-ZSM5-$NH4^+$-600, and $H^+$-BETA-$NH_4^+$-600. Zeolite-Y was directly used without treatment.

After every cycle of isomerization reaction, the spent catalyst needed heat treatment and occasional acid treatment to regain its catalytic activity. Different temperatures and time durations were used as further described herein for the regeneration process depending on the condition of the zeolite. Dry in air treatment was also found effective for a number of cycles, especially in the beginning of the regeneration series. For acid treatment, the previously reported procedure was followed (Ngo, H. L., et al., Eur. J. Lipid Sci. Technol., 114: 213 (2012)).

Reaction procedure: The published reaction procedure (Ngo, H. L., Eur. J. Lipid Sci. Technol., 116: 645 (2014); Ngo, H. L., et al., Eur. J. Lipid Sci. Technol., 114: 213 (2012); U.S. Pat. No. 9,115,076) with modification was followed which can be generally described as follows.

General procedure of isomerization reaction: A mixture of 50 g of oleic acid (OLA), 2.5 g of $H^+$-zeolite catalyst (5.0 w % to OLA), and 0.72 mmol (when used) of Lewis base (TPP, 7.5 w % of zeolite catalyst) was added to a dry 600 mL high pressure stainless steel Parr reactor (Parr Instrument, Moline, Ill.) equipped with a controller and mechanical stirrer. The desired amount of water was also added to the reaction mixture. The reactor was sealed, purged with argon (135 psi, 3×), jacketed with 135 psi argon, and heated at 260° C. for the specified reaction time. After the reaction, the vessel was cooled down to room temperature and the pressure was released. The mixture was diluted with ethyl acetate, filtered under vacuum, and washed with 50 mL of brine solution in a separatory funnel to remove water. The organic layer was dried over 1.0-2.0 g of $Na_2SO_4$ and concentrated in a rotary evaporator to obtain saturated branched-chain fatty acids with other minor products. The spent zeolite received appropriate treatment as disclosed herein before reuse when needed. A general scheme is shown in FIG. 1.

General procedure of hydrogenation reaction: 5 g of sample (unsaturated branched-chain fatty acids) diluted in 20 mL of methanol ($CH_3OH$) was mixed with 500 mg of Pd—C catalyst in a heavy wall glass reactor. The reactor was sealed, placed in a hydrogenator, and purged with hydrogen gas several times. The reaction was carried out under hydrogen for 3 hours with gentle stirring. After the reaction, the reactor was vacuumed and the reaction mixture was filtered by suction filtration through celite and concentrated in a rotary evaporator to obtain saturated branched-chain fatty acid.

General procedure of methylation reaction: The product was methylated for injection into gas chromatography analysis purposes. 200-800 mg of mainly saturated branched-chain fatty acid diluted in 5-15 mL of $CH_3OH$ was added to 100 mg of $H_2SO_4$ in an air tight glass vial. The reaction mixture was heated to 100° C. for 2 hours. The resulting reaction product was then cooled, concentrated in a rotary evaporator, and diluted with 20-40 mL of ethyl acetate. The solution was neutralized two times with saturated aqueous solution of $NaHCO_3$, washed with water, washed with brine solution, and dried over $Na_2SO_4$. The organic layer was concentrated in a rotary evaporator to obtain methyl ester of fatty acids (FAME).

Elemental analysis (EDX) was done with an Oxford Xmax" 80 $mm^2$ detector (Oxford Instruments Tubney Woods Abingdon, Oxfordshire OX13 5QX, United Kingdom). Spectra acquisition and interpretation was performed with AZtec software version 3.1 (Oxford Instruments). Spectra were acquired at 20 KV and spot size 5.

For the BET analysis, the samples were first evacuated using a micromeritics smart-vac prep system in which the samples were kept at 60° C. for 24 hours at 0.005 atm. The BET was then run using a micromeritics 3flex instrument.

Three $NH_4^+$-cationic zeolite based catalytic methods were optimized to obtain high yield of branched-chain fatty acid from unsaturated linear-chain fatty acid (oleic acid). Zeolites-TPP combinations were surprisingly found effective in all three catalytic systems to suppress dimer formation and thus increase the product selectivity as high as 80% with 98% conversion. One of those catalytic systems was tested in ten times larger scale (500 g) production of isostearic acid with 76% selectivity, surprisingly illustrating its sustainability for commercial scale production. Simple procedure for zeolite activation and a complete regeneration technique of the spent zeolite have been proposed based on experimental results to make this technology cost effective. Analysis of fresh and spent zeolites revealed important information about the characteristics of the zeolites to better control the overall skeletal isomerization reaction. Identification of different isomeric composition in products from three zeolites would generate extended application of branched-chain fatty acid.

Example 1: $H^+$-Ferrierite-NH4+

Combinations of reaction parameters were used (Table 1) to test isomerization of oleic acid. The parameters included calcination temperature, reaction time, amount of water (co-catalyst), and amount of base additives (i.e., TPP). The calculation for reaction conversion rate (% Conversion) was based on previously reported technique (Ngo, H. L., Eur. J. Lipid Sci. Technol., 116: 645 (2014)). Overall conversion rate (last column, Table 1) illustrates the total conversion rate for oleic acid to both products (isostearic acid) and byproducts (branched lactones, linear lactones, dimer). Selective conversion is the amount isostearic acid produced (i.e., bc-FAME).

TABLE 1

| Entry | Calcination Temp/Time | TPP (0.72 mmol) & water vol. | Rxn time & temp | bc-FAME % | BL + LL % | Dimer % | % Conversion |
|---|---|---|---|---|---|---|---|
| 1 | 500° C., 5 h | TPP + 1.8 mL | 8 h, 260° C. | 75.6 | 6.3 + 1.8 = 8.1 | 2.2 | 91.3 |
| 2 | 600° C., 24 h | TPP + 1.8 mL | 4 h, 260° C. | 33.2 | 1.8 + 5.9 = 7.7 | 4.3 | 48.1 |
| 3 | 500° C., 5 h | TPP + 1.8 mL | 4 h, 260° C. | 74.6 | 5.3 + 1.9 = 7.2 | 2.1 | 88.8 |
| 4 | 500° C., 5 h | TPP + 1.8 mL | 24 h, 260° C. | 80.9 | 5.9 + 1.1 = 7.0 | 3.9 | 97.4 |
| 5 | 500° C., 5 h | TPP + 1.0 mL | 4 h, 260° C. | 74.3 | 3.5 + 2.2 = 5.7 | 4.0 | 89.1 |
| 6 | 500° C., 5 h | TPP + 1.0 mL | 24 h, 260° C. | 79.9 | 6.4 + 0.9 = 7.3 | 4.8 | 97.7 |
| 7 | 500° C., 5 h | TPP | 8 h, 260° C. | 73.6 | 4.4 + 2.1 = 6.5 | 6.0 | 91.5 |
| 8 | 500° C., 5 h | 1.8 mL | 8 h, 260° C. | 73.1 | 4.9 + 0.7 = 5.6 | 15.4 | 99.9 |
| 9 | 500° C., 5 h | 0 | 8 h, 260° C. | 73.8 | 5.2 + 0.9 = 6.1 | 13.4 | 99.1 |

As the results of Table 1 indicate, a significant range of reaction conversion rate was observed. The conversion dropped from 88.8% to 48.1% (entries 2 and 3, Table 1) when activation parameters were changed from 500° C. for 5 h to 600° C. for 24 h. However, conversion was increased to 99.9% and 99.1%, respectively, without TPP (entries 8 and 9, Table 1) as the starting material was readily consumed to form dimer (13.4-15.4%). Conversion was also increased but insignificantly with the reaction time from 4 h to 24 h (entries 3, 1 and 4, Table 1) along with selectivity (bc-FAME) from 74.6% to 80.9%. Water volume from 1.0 to 1.8 mL had very little effect (entries 3/5 and 4/6, Table 1), but without water the selectivity was reduced with increase of dimer production (entries 1 and 7, Table 1).

Example 2: $H^+$-ZSM5-$NH_4^+$

Combinations of reaction parameters were used (Table 2) to test isomerization of OLA. The parameters included calcination temperature, reaction time, amount of water (co-catalyst), and amount of base additives (i.e., TPP). The calculation for reaction conversion rate (% Conversion) was based on the previously reported technique as in Example 1.

TABLE 2

| Entry | Calcination Temp/Time | TPP (0.72 mmol) & water | Rxn time & temp | bc-FAME % | BL + LL % | Dimer % | % Conversion |
|---|---|---|---|---|---|---|---|
| 1 | 500° C., 5 h | TPP + 1.0 mL | 24 h, 260° C. | 79.6 | 5.3 + 1.6 = 6.9 | 7.2 | 98.2 |
| 2 | 600° C., 24 h | TPP + 1.0 mL | 24 h, 260° C. | 72.5 | 3.3 + 3.1 = 6.4 | 5.6 | 89.8 |
| 3 | 500° C., 5 h | TPP + 1.0 mL | 8 h, 260° C. | 67.1 | 4.2 + 3.9 = 8.1 | 4.8 | 84.9 |
| 4 | 500° C., 5 h | TPP + 1.8 mL | 24 h, 260° C. | 70.6 | 5.5 + 1.6 = 7.1 | 7.5 | 90.4 |
| 5 | 500° C., 5 h | 1.0 mL | 24 h, 260° C. | 67.7 | 2.6 + 2.0 = 4.6 | 22.3 | 100 |
| 6 | 500° C., 5 h | 0 | 24 h, 260° C. | 65.2 | 2.4 + 1.5 = 3.9 | 22.9 | 97.7 |

As shown in Table 2, it was also clear that higher temperature and longer time than 500° C. for 5 h for calcination had an adverse effect on catalyst activity as the conversion dropped from 98.2 to 89.8%, and where the selectivity also dropped from 79.6 to 72.5% (entries 1 and 2, Table 2). Quite surprisingly, this zeolite was found to be not as significantly sensitive toward reaction time, volume of water, and base additives as H$^+$-Ferrierite-NH4+. As the reaction time was cut down from 24 h to 7 h (entries 1 and 3, Table 2), the conversion was diminished from 98.2 to 84.9% with poor selectivity of 67.1%. A similar effect was observed with the addition of more water where the selectivity went down from 79.6 to 70.6% with significant change in conversion (entries 1 and 4, Table 2). Finally, TPP had surprisingly been found to play an important role in suppressing dimer formation and thus increased the selectivity of the reaction (entries 1, 5 and 6, Table 2). Results were improved slightly in reactions with 1 mL of water over dry conditions (entries 5 & 6, Table 2) in terms of both selectivity and conversion.

Example 3: H$^+$-BETA-NH4$^+$

Combinations of reaction parameters were used (Table 3) to test isomerization of OLA. The parameters included calcination temperature, reaction time, amount of water (co-catalyst), and amount of base additives (i.e., TPP). The calculation for reaction conversion rate (% Conversion) was based on the previously reported technique as in Example 1.

resented in entry 1, Table 3 were found as the best combination obtaining the selectivity and conversion of 68.6% and 87.9%, respectively.

Example 4: Large Scale Production of Isostearic Acid

Scale up procedure of isomerization reaction: A mixture of 500 g of oleic acid, 25.0 g of H$^+$-Ferrierite-NH$_4$$^+$ zeolite catalyst, 1.8 g of TPP, and 10.0 mL of distilled water were added to a dry 1 L high pressure stainless steel reactor (Autoclave Engineers, Erie, Pa.). The reactor was sealed, purged with argon (135 psi, 3×), jacketed with 135 psi argon, and heated at 260° C. for 24 h. After the reaction the same work up procedure was followed as described above to obtain ubc-FAs with minimal product loss.

A 10 times larger scale production (500 g) of isostearic acid was achieved using the H$^+$-Ferrierite-NH$_4$$^+$ zeolite under similar reaction conditions (entry 1, Table 1) except reaction time was extended to 24 h instead of 8 h. A duplicate run was carried out to check the reproducibility of the procedure (Table 4). The distribution of the products and

TABLE 3

| Entry | Calcination Temp/Time | TPP (0.72 mmol) & water | Rxn time & temp | bc-FAME % | BL + LL % | Dimer % | % Conversion |
|---|---|---|---|---|---|---|---|
| 1 | 500° C., 5 h | TPP + 0.8 mL | 24 h, 260° C. | 68.6 | 2.2 + 3.1 = 5.3 | 9.0 | 87.9 |
| 2 | 500° C., 5 h | TPP + 1.0 mL | 24 h, 260° C. | 64.5 | 2.9 + 3.8 = 6.7 | 9.7 | 85.7 |
| 3 | 600° C., 24 h | TPP + 1.0 mL | 24 h, 260° C. | 46.0 | 6.3 + 8.3 = 14.6 | 14.5 | 79.5 |
| 4 | 500° C., 5 h | TPP + 0.8 mL | 8 h, 260° C. | 52.9 | 2.9 + 5.9 = 8.8 | 7.2 | 73.3 |
| 5 | 500° C., 5 h | TPP + 1.8 mL | 8 h, 260° C. | 40.0 | 13.7 + 6.3 = 20.0 | 13.2 | 77.7 |
| 6 | 500° C., 5 h | TPP + 1.8 mL | 4 h, 260° C. | 40.9 | 10.4 + 6.8 = 17.2 | 7.4 | 69.7 |
| 7 | 500° C., 5 h | 1.8 mL | 4 h, 260° C. | 53.1 | 9.6 + 3.2 = 12.8 | 17.8 | 88.9 |
| 8 | 500° C., 5 h | 0 | 4 h, 260° C. | 42.5 | 7.3 + 2.1 = 9.4 | 22.7 | 79.2 |

The overall catalytic activities of zeolite H$^+$-BETA-NH$_4$$^+$ were found to depend on calcination temperature/time, reaction duration, volume of water, and the presence of TPP, as illustrated in Table 3. Both the conversion and selectivity were decreased due to the increase of calcination time and temperature from 500° C. to 600° C. (entries 2 and 3, Table 3). There was no significant difference observed from 4 h to 8 h (entries 5 and 6, Table 3) in conversion and also in selectivity until the reaction time was extended to 24 h (entries 1 and 4, Table 3). The volume of water surprisingly played an important role mainly to increase the selectivity by suppressing lactones and dimer formation (entries 4/5 and 1/2, Table 3). In the presence of TPP, the isomerization reaction became slower by saving the starting material from oligomerization to form dimer (entries 6 and 7, Table 3). In this testing for H$^+$-BETA-NH$_4$$^+$ zeolite, the conditions repconversion were surprisingly found very close to the numbers from small scale production (entry 1, Table 1).

TABLE 4

| Run | Calcination Temp/Time | TPP (7.2 mmol) & water | Rxn time & temp | bc-FAME % | BL + LL % | Dimer % | % Conversion |
|---|---|---|---|---|---|---|---|
| 1 | 500° C., 5 h | TPP + 10 mL | 24 h, 260° C. | 76.2 | 7.6 + 2.2 | 4.3 | 96.0 |
| 2 | 500° C., 5 h | TPP + 10 mL | 24 h, 260° C. | 76.1 | 6.7 + 2.3 | 4.7 | 95.4 |

Example 5: Regeneration of Used H$^+$-Ferrierite-NH4$^+$-500 Catalyst

Two series of reactions (shown in Tables 5-A and 5-B) were carried out with different treatments of spent catalysts to establish a systematic catalytic regeneration process. Each series for this example comprised of 10 reaction/regeneration cycles. All the reactions were carried out at 260° C. for 8 hours. All the product yields were calculated by GC analysis after the isomerization reaction, hydrogenation, and methylation. Reactions were carried out with 50 g of oleic acid and 2.5 g of catalyst (5 w % to oleic acid). Methyl tridecanoate was used as internal standard for GC analysis. Fresh H$^+$-Ferr-NH$_4$$^+$ catalyst (SiO$_2$/Al$_2$O$_3$=20 mol/mol)

activated at 500° C. for 5 h was used. UC# indicates catalyst of particular entry number was regenerated. For example, UC1 spent catalyst of entry 1 was regenerated. In this example, only the $H^+$-Ferrierite-$NH_4^+$ catalyst was used to monitor the regeneration process.

From cycles 2 to 4 (entries 12-14, Table 5-B) there was no significant drop in catalytic activity observed; however, at the cycle 5 the selectivity dropped to 55.5% with low conversion of 80.3% (entry 15, Table 5-B) which could not be recovered by the acid treatment or additional TPP. Heat

TABLE 5-A

| Entry | Zeolite ($X^{UC\#}$) | TPP (mmol) + Water (mL) | Treatment | bc-FAME % | BL + LL % | Dimer % | % Conversation |
|---|---|---|---|---|---|---|---|
| 1 | $H^+$-Ferr-$NH_4^+$ | TPP (0.72) + 1.8 mL | — | 75.2 | 6.7 + 1.9 = 8.6 | 2.4 | 91.8 |
| 2 | $2^{UC1}$ | 1.8 mL $H_2O$ | 120° C. for 3 h | 72.8 | 3.8 + 2.9 = 5.7 | 3.5 | 88.3 |
| 3 | $3^{UC2}$ | 1.8 mL $H_2O$ | 120° C. for 3 h | 75.1 | 6.4 + 0.9 = 7.5 | 9.9 | 98.0 |
| 4 | $4^{UC3}$ | 1.8 mL $H_2O$ | 120° C. for 3 h | 67.5 | 3.3 + 2.9 = 6.2 | 9.4 | 88.3 |
| 5 | $5^{UC4}$ | TPP (0.48) + 1.8 mL $H_2O$ | 120° C. for 3 h | 51.1 | 2.4 + 5.6 = 8.0 | 4.2 | 67.2 |
| 6 | $6^{UC5}$ | TPP (0.48) + 1.8 mL $H_2O$ | 0.1N HCl & 120° C. for 3 h | 62.3 | 2.9 + 4.7 = 7.6 | 2.1 | 76.5 |
| 7 | $7^{UC6}$ | TPP (0.48) + 1.8 mL $H_2O$ | 1.0N HCl & 120° C. for 3 h | 63.9 | 3.7 + 4.1 = 7.8 | 2.7 | 78.9 |
| 8 | $8^{UC7}$ | 1.8 mL $H_2O$ | 500° C. for 5 h | 74.3 | 4.5 + 0.8 = 5.3 | 11.9 | 97.1 |
| 9 | $9^{UC8}$ | TPP (0.72) + 1.8 mL $H_2O$ | Dry in air | 68.1 | 3.0 + 3.2 = 6.2 | 3.3 | 82.4 |
| 10 | $10^{UC9}$ | TPP (0.72) + 1.8 mL $H_2O$ | 500° C. for 5 h | 74.2 | 3.4 + 1.5 = 4.9 | 5.1 | 89.4 |

TABLE 5-B

| Entry | Zeolite ($X^{UC\#}$) | TPP (mmol) + Water (mL) | Treatment | bc-FAME % | BL + LL % | Dimer % | % Conversation |
|---|---|---|---|---|---|---|---|
| 11 | $H^+$-Ferr-$NH_4^+$ | TPP (0.72) + 1.8 mL | — | 75.6 | 6.3 + 1.8 = 8.1 | 2.2 | 91.3 |
| 12 | $12^{UC11}$ | 1.8 mL $H_2O$ | Dry in air | 71.2 | 3.5 + 3.1 = 6.6 | 5.0 | 87.9 |
| 13 | $13^{UC12}$ | 1.8 mL $H_2O$ | Dry in air | 73.2 | 7.7 + 1.1 = 8.8 | 11.0 | 98.8 |
| 14 | $14^{UC13}$ | 1.8 mL $H_2O$ | Dry in air | 73.2 | 5.7 + 1.2 = 6.9 | 11.7 | 97.4 |
| 15 | $15^{UC14}$ | 1.8 mL $H_2O$ | Dry in air | 55.5 | 3.2 + 4.4 = 7.6 | 12.6 | 80.3 |
| 16 | $16^{UC15}$ | TPP (0.48) | 1.0N HCl & 120° C. for 3 h | 33.2 | 1.9 + 7.0 = 8.9 | 3.8 | 48.7 |
| 17 | $17^{UC16}$ | 1.8 mL $H_2O$ | 500° C. for 5 h | 73.9 | 3.7 + 1.6 = 5.3 | 10.6 | 95.4 |
| 18 | $18^{UC17}$ | TPP (0.72) + 1.8 mL $H_2O$ | Dry in air | 53.6 | 3.9 + 5.3 = 9.2 | 4.5 | 71.5 |
| 19 | $19^{UC18}$ | TPP (0.72) + 1.8 mL $H_2O$ | 500° C. for 5 h | 66.8 | 2.8 + 3.9 = 6.7 | 3.9 | 82.2 |
| 20 | $20^{UC19}$ | TPP (0.72) + 1.8 mL $H_2O$ | 500° C. for 5 h | 62.2 | 1.9 + 5.3 = 7.2 | 3.9 | 77.9 |

In series 1 (Table 5-A), the spent catalyst was regenerated by heating at 120° C. for 3 h in the first three cycles (entries 2-4, Table 5-A,), where the conversion and selectivity were slightly lower with significant increase in dimer formation from 2.4%-9.4%. In the next cycle (entry 5, Table 5-A,), addition of TPP was found effective to suppress dimerization but was not useful in increasing reaction conversion rate or selectivity. At that point two successive acid treatments of catalyst were carried out (entries 5-6, Table 5-A) which improved its efficiency but not at a satisfactory level. Eventually, heat treatment at 500° C. for 5 h restored its catalytic performance (entry 8, Table 5-A) as close to new with significant amount of dimer formation which ultimately pushed the reaction conversion rate as high as 97.1%. Dimer formation was also controlled at this stage by the additional amount of TPP to obtain high selectivity of 74.2% (entry 10, Table 5-A).

In series 2 (Table 5-B), the spent catalyst was regenerated by drying in air up to four cycles (entries 12-15, Table 5-B).

treatment at 500° C. for 5 h successfully restored the catalyst close to its original performance (entry 17, Table 5-B). At this stage, although air drying was found ineffective to regenerate the catalyst, dimer formation could still be quenched by the additional TPP (entry 18, Table 5B).

Example 6: Catalyst Characterization

Thermogravimetric analysis (TGA) experiments were performed on a Q500-1708 TGA Q500 instrument. Samples were run with platinum cell holders. A 10-20 mg sample was run from 25 to 900° C. at 10° C./min. The sample purge flow was set at 60 mL/min in nitrogen and the balance purge flow was set at 40 mL/min in air. TGA analysis of mass loss (wt. %) from fresh and spent zeolites was performed. Catalyst samples $H^+$-Ferrierite-$NH_4^+$-500, $H^+$-Ferrierite-$NH_4^+$-600, $H^+$-ZSM5-$NH_4^+$-500, $H^+$-ZSM5-$NH_4^+$-600, $H^+$-BETA-$NH_4^+$-500, $H^+$-BETA-$NH_4^+$-600, and spent zeolites after cycle 10 in each series (entries 10 and 20, Tables 5A-5B) of $H^+$-Ferrierite-$NH_4^+$-500 regeneration were selected for full characterization. Results are presented in Table 6.

TABLE 6

| Entry | Catalyst | % Wt. loss region 1 (25-250° C.) | % Wt. loss region 2 (250-400° C.) | % Wt. loss region 3 (400-700° C.) |
| --- | --- | --- | --- | --- |
| 1 | $H^+$-Ferrierite-$NH_4^+$-500 | 7.9 | 0.2 | 0.5 |
| 2 | $H^+$-Ferrierite-$NH_4^+$-600 | 5.8 | 0.4 | 0.3 |
| 3 | $H^+$-ZSM5-$NH_4^+$-500 | 8.8 | 0.4 | 0.5 |
| 4 | $H^+$-ZSM5-$NH_4^+$-600 | 5.6 | 0.3 | 0.2 |
| 5 | $H^+$-BETA-$NH_4^+$-500 | 11.7 | 0.5 | 0.7 |
| 6 | $H^+$-BETA-$NH_4^+$-600 | 5.9 | 0.4 | 0.3 |
| 7 | Spent zeolites-$10^{UC9}$-500** | 5.3 | 0.5 | 0.2 |
| 8 | Spent zeolites-$20^{UC19}$* | 13.3 | 1.8 | 1.6 |
| 9 | Spent zeolites-$20^{UC19}$-500** | 5.4 | 0.3 | 0.3 |

*Spent zeolite was collected after drying in air
**Spent zeolite was analyzed after heating at 500° C. for 5 h TGA showed three successive regions of weight loss for most of the zeolites. The biggest loss was observed from room temperature to 250° C., which was mostly due to water loss or trace amounts of organic solvent in case of spent zeolites (entry 8, Table 6). No significant differences were found in the last two regions (wt. loss regions 2 and 3) between the particular fresh zeolites which were calcined at 500° C. for 5 h or 600° C. for 24 h. An important weight loss of 1.8% was detected in the region 2 for spent zeolite without heat treatment (entry 8, Table 6) with further loss of 1.6% in the region 3. However, in case of spent zeolites with heat treatment at 500° C. for 5 h (entries 7 and 9, Table 6) the losses were comparable to that from particular fresh zeolite (entry 1, Table 6) in the last two regions but lesser loss in region 1 indicating more dehydrated condition.

TGA further detected more dry conditions in zeolites calcined at higher temperature (entries 2, 4, and 6, Table 6) and also in spent zeolites (entries 7 and 9, Table 6). Spent untreated zeolite (entry 8, Table 6) was found to contain reaction residue identified by weight loss in the second and third regions of TGA analysis. This residue could be almost removed by heating at 500° C. for 5 h (entry 9, Table 6). This result was further supported by BET surface area, pore volume measurement and FTIR analysis (discussed below).

Figure 2A:
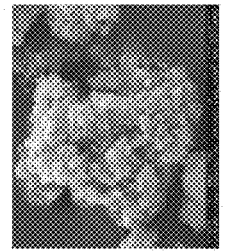
FIG. 2A-2J show SEM patterns of fresh (A-G) and spent (H-J) zeolite samples as described below.
Figure 2B:
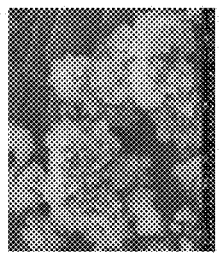
Figure 2C:
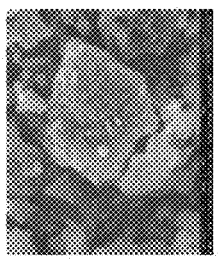
Figure 2D:
Figure 2E:
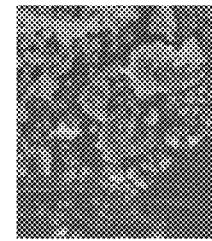
Figure 2F:
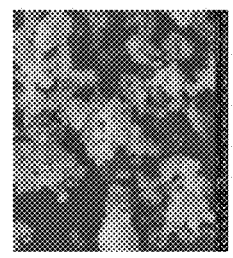
Figure 2G:
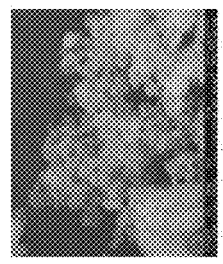
Figure 2I:

For Scanning Electron Microscopy (SEM) analysis, samples were mounted on carbon stubs (SPI West Chester, Pa.) and sputter gold coated for 1 minute (EMS 150R ES, EM Sciences, Hatfield, Pa.). Samples were viewed with a FEI Quanta 200 F Scanning Electron Microscope, (Hillsboro, Oreg.) with an accelerating voltage of 10 KV in high vacuum mode. The images with scale bars of 2.0 µm (FIG. 2A-2F) and 5.0 µm (FIG. 2G-2J) are displayed. Comparison of SEM images of differently calcined fresh zeolites (FIGS. 2A-2B, 2C-2D, and 2E-2F) indicated that there were minimal differences between the morphology and crystal shapes. The spent zeolite sample without any treatment (FIG. 2I) appeared chunkier than its corresponding fresh zeolite sample (FIG. 2G). However, this chunkiness disappeared due to the heat treatment at 500° C. for 5 h (FIG. 2J).

According to the SEM images (FIG. 2H, 2J) it was important to observe that after using used in ten cycles the size of the zeolite crystals became smaller than the original (FIG. 2G).

To obtain a quantitative comparison, particle size distribution analysis was carried out. In this study, the obtained SEM images were processed using ImageJ software. Developed at the National Institutes of Health (NIH), ImageJ is a Java-based public domain image processing and analysis program, which was used to measure the particle size and size distribution of the samples. Four zeolite samples including $H^+$-Ferrierite-$NH_4^+$-500, $H^+$-Ferrierite-$NH_4^+$-600, spent zeolites-$10^{UC9}$-500, and spent zeolites-$20^{UC19}$-500 were analyzed to obtain their particle size distribution (FIG. 3). Data was collected at every 5 square microns in between 0-100 microns. From FIG. 3, a significant change was visible in particle size distribution between the samples $H^+$-Ferrierite-$NH_4^+$-500 and $H^+$-Ferrierite-$NH_4^+$-600, indicating strong impact on particle size reduction due to the increase of calcination temperature and time. Another distinctive particle size reduction was observed between the fresh and spent zeolites. Spent zeolites-$10^{UC9}$-500 and spent zeolites-$20^{UC19}$-500 were found in less quantity with big size particles (30 square microns or above) than their starting fresh zeolite of $H^+$-Ferrierite-$NH_4^+$-500.

Energy Dispersive Spectroscopy (EDS) provided the elemental analysis (e.g., O, Al, Si, etc.) and their relative proportions in the samples. The output of EDS analyses of the zeolite samples are listed in Table 7 and showed strong elemental signal of oxygen, silicon, and aluminum. The Si/Al ratios of ZSM5 (entries 3-4, Table 7) and BETA (entries 5-6, Table 7) zeolites were found close enough to 11.5 and 12.5 respectively as previously reported (Zhang, L., et al., J. Am. Chem. Soc., 137: 11810 (2015)). It was important to find that the Si/Al ratio of zeolite samples remained mostly unchanged (±1) at different calcination temperatures and after isomerization reaction (entries 1 and 7-9, Table 7) as expected.

TABLE 7

| Entry | Zeolite Catalyst | Si (Wt. %) | Al (Wt. %) | O (Wt. %) | Ratio (Si/Al) |
| --- | --- | --- | --- | --- | --- |
| 1 | $H^+$-Ferrierite-$NH_4^+$-500 | 28.3 | 3.1 | 68.7 | 9.1 |
| 2 | $H^+$-Ferrierite-$NH_4^+$-600 | 28.6 | 3.1 | 68.3 | 9.2 |
| 3 | $H^+$-ZSM5-$NH_4^+$-500 | 30.0 | 2.7 | 67.3 | 11.1 |
| 4 | $H^+$-ZSM5-$NH_4^+$-600 | 28.0 | 2.7 | 69.3 | 10.4 |
| 5 | $H^+$-BETA-$NH_4^+$-500 | 28.1 | 2.6 | 69.3 | 10.8 |
| 6 | $H^+$-BETA-$NH_4^+$-600 | 28.8 | 2.6 | 68.6 | 11.0 |
| 7 | Spent zeolites-$10^{UC9}$-500** | 27.0 | 2.8 | 70.0 | 9.6 |

TABLE 7-continued

| Entry | Zeolite Catalyst | Si (Wt. %) | Al (Wt. %) | O (Wt. %) | Ratio (Si/Al) |
|---|---|---|---|---|---|
| 8 | Spent zeolites, $20^{UC19}$* | 25.1 | 2.7 | 72.2 | 9.2 |
| 9 | Spent zeolites, $20^{UC19}$-500** | 26.0 | 2.7 | 71.3 | 9.6 |

*Spent zeolite was collected after drying in air
**Spent zeolite was analyzed after heating at 500° C. for 5 h PXRD patterns were recorded at 20° C. on a Bruker D8 venture X-ray diffractometer with a scintillation counter and a graphite mono-chromator attachment, using Copper X-ray source with a wavelength of 1.54 angstroms. Powder X-ray diffraction analysis was used to determine the morphologies and degree of crystallinity of zeolites. A 2 theta range of 00 to 500 is usually enough to cover the most important regions of XRD pattern. The sharpness and relative intensities of the peaks are related to the level of crystallinity and orientation which are determined by the type and position of all atoms in the cell, whereas amorphous sample shows broad diffused peak. Generally in XRD pattern, the flat base line, the peak in the range of 2 theta=20-35° and narrow peaks are indicatives of crystalline samples (Pedrosa, A. M. G., et al., Mater. Res. Bull., 41(6): 1105 (2006); Yu, H., et al., J. Colloid Interface Sci., 428: 251 (2014); Katada, N., et al., J. Mole. Catal. A: Chem., 211(1-2): 119 (2004)).

FIG. 4A-4D shows the XRD pattern of zeolites, where FIG. 4A shows H$^+$-Ferrierite-NH4$^+$-500 and 600; FIG. 4B shows H$^+$-ZSM5-NH4$^+$-500 and 600; FIG. 4C shows H$^+$-BETA-NH4$^+$-500 and 600; and FIG. 4D shows Fresh H$^+$-Ferrierite-NH4$^+$-500, Spent zeolites-10$^{UC9}$-500, and Spent zeolites, $20^{UC19}$-500. The intensity of peaks decreased when NH4$^+$-Ferrierite was calcined at 600° C. for 24 h instead of 500° C. for 5 h. Similarly in the case of NH4$^+$-ZSM-5, a lower level of crystallinity was detected by uneven base line (FIG. 4B) when calcined at elevated temperature. No significant difference was observed for NH4$^+$-BETA catalyst calcined at either temperature, but they were found less crystalline or mixed with amorphous materials illustrated by the broad peaks and uneven base line (FIG. 4C). On the other hand, the crystallinity of the spent zeolites after 10 cycles of reaction remained either similar or slightly decreased which could be confirmed by the reduced intensity (FIG. 4D).

BET surface areas and total pore volumes of the 9 zeolite samples are listed in Table 8. A slight increase in surface area and pore volume were observed due to higher and longer calcination temperature and time in cases of all three zeolites (entries 1-6, Table 8), but such a little gain should be insignificant to change the activity of zeolites in isomerization reaction of oleic acid. The BET surface area of the spent zeolite (entry 7, Table 8) used in 10 cycles of reaction was 216 m$^2$/g which was a meaningful drop from the initial fresh zeolite with surface area of 354 m$^2$/g (entry 1, Table 8). In case of spent zeolite without heat treatment, the BET surface area went down to 6.8 m$^2$/g (entry 8, Table 8), and also the total pore volume dropped to 0.0703 cm$^3$/g which indicated that the cavity of the zeolites were almost fully occupied by the reaction residues. However, both the surface area and pore volume were improved to 227 m$^2$/g and 0.1839 cm$^3$/g, respectively, (entry 9, Table 8) by heating at 500° C. for 5 h.

The BET surface area increased from 6.8 m$^2$/g to 227 m$^2$/g when spent untreated zeolite was heated at 500° C. for 5 h (entries 8 and 9, Table 8), whereas total pore volume went up from 0.0703 to 0.1839 cm$^3$/g which was very close to fresh zeolite of 0.1966 cm$^3$/g (entry 1, Table 8). The FTIR showed (FIG. 5) four additional peaks at 1715, 2860, 2930, and 2960 cm$^{-1}$ which were identified in a previous article (Wiedemann, S. C., et al., Journal of Catalysis, 316: 24 (2014)) as the residue of long chain fatty acid or dimer acid and disappeared by the regeneration treatment at 500° C. From this analysis, it could be summarized that 500° C. for 5 h was sufficient to restore the catalytic activity of zeolite even after ten cycles.

TABLE 8

| Entry | Zeolite Catalyst | BET surface area m$^2$/g | Pore Volume (cm$^3$/g) |
|---|---|---|---|
| 1 | H$^+$-Ferrierite-NH4$^+$-500 | 354 | 0.1966 |
| 2 | H$^+$-Ferrierite-NH4$^+$-600 | 373 | 0.2099 |
| 3 | H$^+$-ZSM5-NH4$^+$-500 | 375 | 0.1996 |
| 4 | H$^+$-ZSM5-NH4$^+$-600 | 388 | 0.2085 |
| 5 | H$^+$-BETA-NH4$^+$-500 | 509 | 0.6949 |
| 6 | H$^+$-BETA-NH4$^+$-600 | 547 | 0.7714 |
| 7 | Spent zeolites-10 $^{UC9}$-500** | 216 | 0.1724 |
| 8 | Spent zeolites, $20^{UC19}$* | 6.8 | 0.0703 |
| 9 | Spent zeolites, $20^{UC19}$-500** | 227 | 0.1839 |

*Spent zeolite was collected after drying in air
**Spent zeolite was analyzed after heating at 500° C. for 5 h FTIR spectra of the zeolites samples were recorded on a FT-IR spectrometer (Thermo NEXUS 670 Near-, Far- and Mid-FTIR with ATR) equipped with a DTGS detector. The spectra of the film on KBr (128 scans) were recorded at RT between 4000 and 400 cm$^{-1}$, with a special resolution of 4 cm$^{-1}$.

Figure 5:
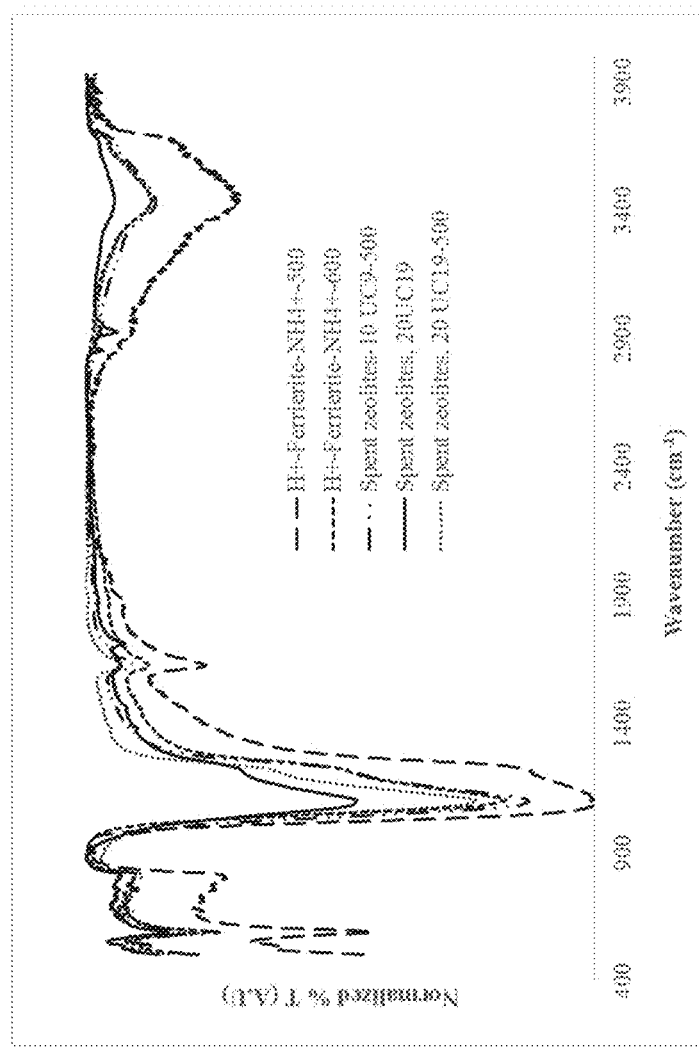
FIG. 5 shows FTIR spectra of fresh and spent zeolite catalysts as described below.

FTIR spectroscopy analyses were performed on five zeolite samples (H$^+$-Ferrierite-NH4$^+$-500, H$^+$-Ferrierite-NH4$^+$-600, spent zeolites-10$^{UC9}$-500, spent zeolites, $20^{UC19}$, and spent zeolites, $20^{UC19}$-500) to determine the changes caused by the differences in calcination conditions and repeated isomerization reactions. The FTIR spectra are shown in FIG. 5. The band in the range of 1050 cm$^{-1}$ to 1250 cm$^{-1}$ corresponded to internal vibration of M-O-M (M=Si, Al) tetrahedral structures. The vibration band at 1630 cm$^{-1}$ was assigned to bending vibration of adsorbed water molecule (H—O—H bending) and the band with a peak at 3444 cm$^{-1}$ was assigned to OH stretching. The FTIR results indicated that the position of each peak was nearly identical for all the samples except spent zeolites $20^{UC19}$ where some additional peaks were identified at 1715, 2860, 2930, and 2960 cm$^{-1}$. These peaks were indicative of the presence of long chain fatty acid and/or dimer fatty acids. The peak at 1715 cm$^{-1}$ was attributed to C=O stretching of carboxylic group, whereas the long aliphatic carbon chain was represented by the peaks at 2860 cm-1 ($v_{sym}$ CH$_2$), 2930 cm$^{-1}$ ($v_{asym}$ CH$_2$), and 2960 cm$^{-1}$ ($v_{asym}$ CH$_3$) (Wiedemann, S. C., et al., Journal of Catalysis, 316: 24 (2014)).

All the reaction products were also quantified with gas chromatography HP5890 series II Gas Chromatograph with 7673 auto-sampler in the form of fatty acid methyl ester (FAME). GC analysis of FAME products was carried out with an Agilent 7890B (GC) (Agilent, Wilmington, Del.)

equipped with a capillary column (on-column mode) and a FID detector. The GC capillary column used was a DB-5HT (30 m×320 μm×0.1 μm) attached to an Alltech Co. deactivated fused silica guard column (3 m×0.32 μm) with He carrier gas set at a linear velocity of 22 cm/s at 100° C. The oven temperature profile was set at an initial temperature of 50° C., ramped at 15° C./min to 160° C., ramped at 7° C./min to 230° C., ramped at 30° C./min to 380° C., and held 10 minutes.

To obtain better separation of the isomeric mixture of products (discussed below), the GC was equipped with a standard oven for temperature programming, split/splitless injection ports, and a flame ionization detector (FID). Separations were performed with a Phenomenex (Torrance, Calif.) Zebron ZB-5HT capillary column (30 m×0.25 mm i.d.×0.25 um coating thickness) which consisted of 5% cyanopropyl phenyl and 95% dimethyl polysiloxane as stationary phase. Injector and detector temperatures for the FID were set to 270° C. and 280° C., respectively. He column gas flow rate remained constant at 1.0 mL/min during the entire analysis. 20 μL of all samples were diluted with 1.0 ml ethyl acetate before analysis. 1 μL of sample solutions was injected in the GC injection port. Direct injections were performed in split mode with a 5:1 split ratio using the following temperature program: initial temperature 70° C. held for 2 min, ramped at 30° C./min to 175° C., and finally ramped at 0.3° C./min to 185° C.

GC/MS characterization of FAME was carried out attaching a capillary inlet (split mode) and 5975c inert electron and chemical MS detector (XL EL/Cl MSD). The mass detector was set to scan from 40 to 550 m/z at a rate of 1.5 scans/s. The capillary column used was a DB-5HT (30 m×0.25 mm×0.1 μm) with the He carrier gas set at a linear velocity of 22 cm/s at 100° C. The injector and detector transfer line temperatures were set at 250 and 280° C. respectively. The oven temperature profile was as follows: initial temperature 50° C. held for 2 minutes; ramped at 15° C./min to 150° C., ramped at 7° C./min to 200° C.; ramped at 30° C./min to 350° C. and held for 12 minutes.

Figure 6A:
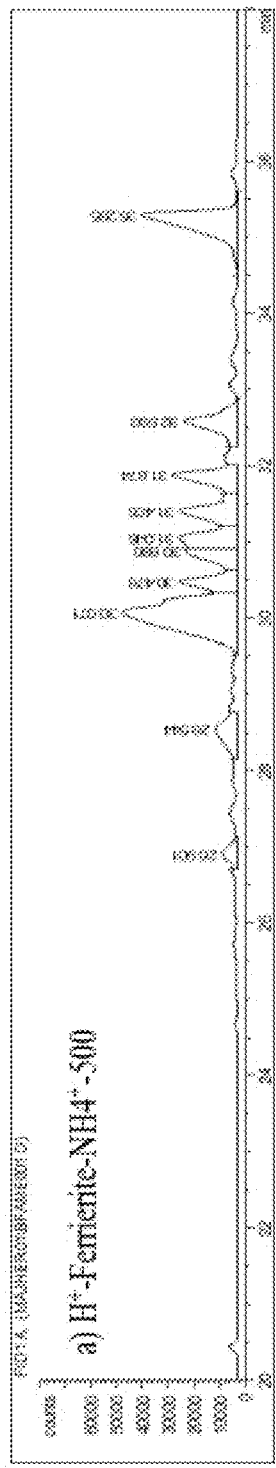
FIG. 6A-6C show GC chromatographs of branched-chain isomers (bc-FAMEs) produced from the catalytic methods as described below.
Figure 6B:
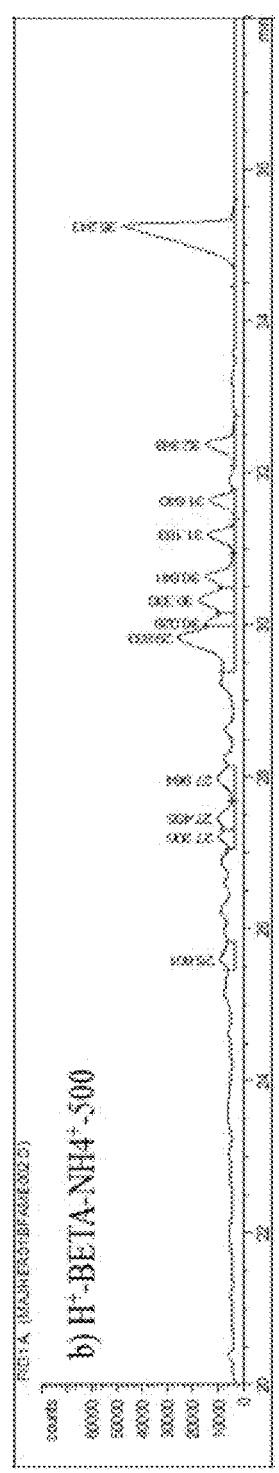
Figure 6C:
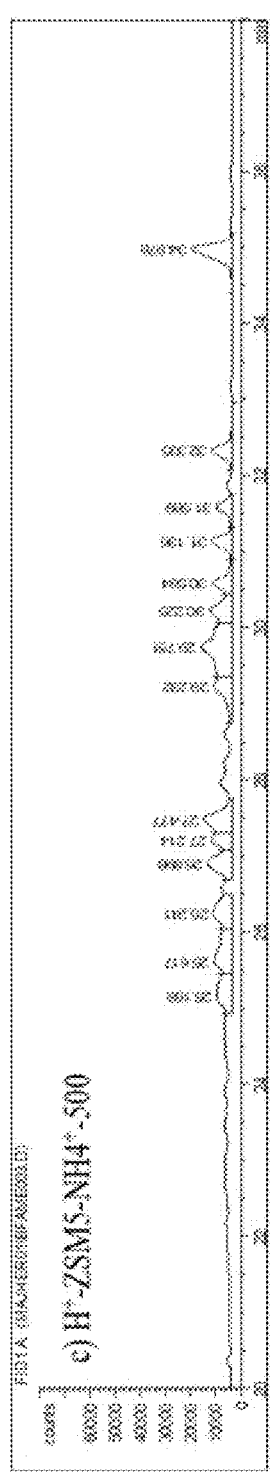

Variation in isomeric mixture of products from different catalysts was observed via gas chromatograms of methyl ester of isostearic acid products (FAME) produced from three optimized zeolite based catalytic methods are shown in FIG. 6A-6C. A modified GC method was used to obtain better separation among branched isomers of FAME. It can be seen in FIG. 6 that the relative ratio for the branched isomers was different in three individual spectra. For example, in FIG. 6A, the isomer or mixture of isomers eluted at 30 minutes was present in a higher ratio (in comparison to other isomers) than in other two product mixtures (FIG. 6B-6C). On the other hand in FIG. 6C, more isomers were found to be eluted at retention time 25-28 minutes than in other products. Although individual structural characterization of these isomers was not performed, research efforts to determine those isomers are ongoing and will be published in due course.

Example 7

$H^+$-zeoliteY ($SiO_2/Al_2O_3$=80) was used to demonstrate the effect of Si/Al ratio in skeletal isomerization reactions on a 50 g scale as above. Optimized reaction conditions for particular zeolytic system have been established to understand their reaction mechanism and to achieve the best performance. Low conversion and selectivity from $H^+$-zeolite Y was mainly due to the lack of active sites in the zeolite (Table 9).

TABLE 9

| Zeolite | Activation Temp | TPP (7.2 mmol) & water | Rxn time & temp | bc-FAME % | BL + LL % | Dimer % | % Conversion |
|---|---|---|---|---|---|---|---|
| $H^+$-zeolite Y | — | TPP + 1.8 mL | 24 h, 260° C. | 20.1 | 1.1 + 7.5 | 15.3 | 46.8 |

Zeolite catalytic methods were tested for skeletal isomerization reaction to produce branched-chain fatty acids (e.g., isostearic acid) from unsaturated linear chain fatty acid with surprisingly high levels of selectivity and conversion. The $SiO_2/Al_2O_3$ molar ratio of zeolite, calcination temperature, amount of co-catalyst and additives were found as key factors for the reactivity of zeolites in these particular reactions. To be cost effective, heat treatment was mainly used for catalytic activation and regeneration of used catalyst. A full scale characterization of fresh and spent zeolites confirmed the surprising sustainability of zeolite catalysts even after multiple uses in the illustrated isomerization reactions. Dimer production due to interaction with the external acidic surface of the zeolites was observed and can be suppressed.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

The term "consisting essentially of" excludes additional method (or process) steps or composition components that substantially interfere with the intended activity of the method (or process) or composition. This term may be substituted for inclusive terms such as "comprising" or "including" to more narrowly define any of the disclosed embodiments or combinations/sub-combinations thereof.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The invention claimed is:

1. A process for converting an unsaturated fatty acid into a saturated branched-chain fatty acid and/or alkyl ester(s) thereof, the process comprising: (a) subjecting the unsaturated fatty acid to a skeletal isomerization reaction at a temperature from about 200° C. to 280° C. for a time range from about 4 to about 24 hours to result in a selective conversion of the unsaturated fatty acid into the saturated branched-chain fatty acid and/or alkyl ester(s) thereof, the skeletal isomerization reaction occurring in the presence of (i) an activated zeolite catalyst, wherein a zeolite catalyst is calcined at a temperature from about 400° C. to about 600° C. for about 1 hour to about 10 hours in a furnace to convert the zeolite catalyst into the activated zeolite catalyst, (ii) an effective amount of water or a lower alcohol to improve the selective conversion of the unsaturated fatty acid into the saturated branched-chain fatty acid and/or alkyl ester(s) thereof, and (iii) optionally an oligomerization reducing agent; (b) recovering an organic layer and subjecting the organic layer to a hydrogenation step to produce a product including the saturated branched-chain fatty acid; (c) recovering a spent zeolite catalyst; and (d) regenerating the spent zeolite catalyst by heating the spent zeolite to a temperature of about 120° C. to about 500° C. for a time of about 3 hours to about 5 hours to create a regenerated zeolite catalyst that is functional for use as the activated zeolite catalyst; wherein the zeolite catalyst is converted to the activated zeolite catalyst and the spent zeolite catalyst is converted to the regenerated zeolite catalyst without an acid treatment step.

2. The process of claim 1, wherein the unsaturated fatty acid is an unsaturated linear chain fatty acid.

3. The process of claim 1, wherein the unsaturated fatty acid has a carbon chain length from 12 to 30 carbon atoms.

4. The process of claim 1, wherein the unsaturated fatty acid has a carbon chain length from 12 to 24 carbon atoms.

5. The process of claim 1, wherein the unsaturated fatty acid has a carbon chain length from 16 to 20 carbon atoms.

6. The process of claim 1, wherein the unsaturated fatty acid is an unsaturated linear chain fatty acid derived from a renewable source.

7. The process of claim 1, wherein the unsaturated fatty acid is an unsaturated linear chain fatty acid derived from a renewable source selected from the group consisting of: vegetable oil(s), animal fat(s), industrial byproduct(s), and combinations thereof.

8. The process of claim 1, wherein the unsaturated fatty acid is oleic acid.

9. The process of claim 1, wherein the selective conversion results in at least about 65% to about 85% selective conversion of the unsaturated fatty acid into the saturated branched-chain fatty acid alkyl ester(s) thereof.

10. The process of claim 1, wherein the saturated branched-chain fatty acid is mainly isostearic acid mixed with other saturated branched-chain fatty acids depending on feedstock.

11. The process of claim 1, wherein subjecting the unsaturated fatty acid to the skeletal isomerization reaction occurs at a temperature from about 240° C. to about 260° C.

12. The process of claim 1, wherein subjecting the unsaturated fatty acid to the skeletal isomerization reaction occurs at a temperature of about 260° C.

13. The process of claim 1, wherein the furnace is a muffle furnace.

14. The process of claim 1, wherein the zeolite catalyst is selected from the group consisting of: $NH_4^+$-Ferrierite; $NH_4^+$-ZSM-5; $NH_4^+$-BETA; and any combination thereof.

15. The process of claim 1, wherein the zeolite catalyst is selected from the group consisting of: $NH_4^+$-Ferrierite with a $SiO_2/Al_2O_3$ ratio of 20; $NH_4^+$-ZSM-5 with a $SiO_2/Al_2O_3$ ratio of 23; $NH_4^+$-BETA with a $SiO_2/Al_2O_3$ ratio of 25; and any combination thereof.

16. The process of claim 1, wherein the zeolite catalyst has a $SiO_2/Al_2O_3$ ratio from about 17 to about 25.

17. The process of claim 1, wherein the zeolite catalyst has a $SiO_2/Al_2O_3$ ratio from about 20 to about 25.

18. The process of claim 1, wherein the zeolite catalyst is converted into the activated zeolite catalyst at a temperature from about 400° C. to about 500° C.

19. The process of claim 1, wherein the zeolite catalyst is converted into the activated zeolite catalyst at a temperature of about 450° C. to about 500° C.

20. The process of claim 1, wherein the oligomerization reducing agent is selected from the group consisting of: amine; phosphine; triarylphosphine; dialkylarylphosphine; trialkylphosphine; and any combinations or mixtures thereof.

21. The process of claim 20, wherein the amine is selected from the group consisting of: dimethylamine; trimethylamine; diethylamine; trimethylamine; diisopropylamine; triisopropylamine; triphenylamine; diphenylamine; and any combinations or mixtures thereof.

22. The process of claim 20, wherein said phosphine is selected from the group consisting of: methylphosphine; butylphosphine; dibutylphosphine; tributylphosphine; phenylphosphine; diphenylphosphine; and any combinations or mixtures thereof.

23. The process of claim 20, wherein said triarylphosphine is selected from the group consisting of: triphenylphosphine; tri-p-tolylphosphine; tri(o-tolyl)phosphine; tri-m-tolylphosphine; trixylyl-phosphine, tris(p-ethylphenyl)phosphine, tris(p-methoxyphenyl)phosphine, tris(4-fluorophenyl)phosphine; tris(4-methoxyphenyl)phosphine; tris(dimethylamino)phosphine; tris(trimethylsilyl)phosphine; triisopropylphosphine; and any combinations or mixtures thereof.

24. The process of claim 20, wherein the dialkylarylphosphine is selected from the group consisting of: di-n-butyl-phenylphosphine; dicyclohexylphenylphosphine; and any combinations or mixtures thereof.

25. The process of claim 20, wherein the trialkylphosphine is selected from the group consisting of: tri-n-butylphosphine; tricyclohexylphosphine; tri-n-octylphosphine; trimethyphosphine; triethylphosphine; triisopropylphosphine; tricyclopentylphosphine; and any combinations or mixtures thereof.

26. The process of claim 1, wherein the oligomerization reducing agent is triphenylphosphine.

27. The process of claim 1, wherein regenerating the spent zeolite catalyst by heating the spent zeolite to a temperature of about 120° C. to about 500° C. for a time of about 3 hours to about 5 hours to create the regenerated zeolite catalyst that is functional for use as the activated zeolite catalyst is performed for at least about 10 cycles.

28. A method of regenerating a zeolite catalyst, the method comprising: recovering a spent zeolite catalyst and regenerating the spent zeolite catalyst without the use of an acid treatment step by heating the spent zeolite catalyst to a temperature of about 120° C. to about 500° C. for a time of about 3 hours to about 5 hours to create a regenerated zeolite catalyst that is functional for use as an activated zeolite catalyst.

29. The method of claim 28, further comprising (a) calcining the zeolite catalyst at a temperature from about 500° C. to about 600° C. to create the activated zeolite catalyst; (b) using the activated zeolite catalyst in a skeletal isomerization reaction to convert an unsaturated fatty acid into a saturated branched-chain fatty acid and/or alkyl ester(s) thereof to create reaction products and the spent zeolite catalyst.

30. The method of claim 28, wherein the zeolite catalyst is selected from the group consisting of: $NH4^+$-Ferrierite; $NH4^+$-ZSM-5; $NH4^+$-BETA; and any combination thereof.

* * * * *